United States Patent
Ingall et al.

(10) Patent No.: US 6,890,923 B2
(45) Date of Patent: May 10, 2005

(54) COMPOUNDS

(75) Inventors: Anthony Howard Ingall, Leicestersire (GB); John Raymond Bantick, Leicestershire (GB); Matthew William Dampier Perry, Leicestershire (GB)

(73) Assignee: AstraZeneca AB, Sodertalje (SE)

( * ) Notice: Subject to any disclaimer, the term of this patent is extended or adjusted under 35 U.S.C. 154(b) by 24 days.

(21) Appl. No.: 10/319,847

(22) Filed: Dec. 16, 2002

(65) Prior Publication Data

US 2004/0122028 A1 Jun. 24, 2004

(51) Int. Cl.$^7$ .................... C07D 495/04; A61K 31/519; A61P 37/06; A61P 11/06; A61P 11/08
(52) U.S. Cl. ............................ 514/234.2; 514/260.1; 544/278; 544/117
(58) Field of Search ............... 544/278; 514/234.2, 514/260.1

(56) References Cited

U.S. PATENT DOCUMENTS

| | | | |
|---|---|---|---|
| 6,180,635 B1 * | 1/2001 | Cheshire et al. | 514/260.1 |
| 2004/0014634 A1 * | 1/2004 | Bantick et al. | 514/1 |
| 2004/0180873 A1 * | 9/2004 | Hanssen et al. | 514/210.21 |
| 2004/0180907 A1 * | 9/2004 | Hanssen et al. | 544/281 |

FOREIGN PATENT DOCUMENTS

| | | | | |
|---|---|---|---|---|
| GB | 2363377 A | * | 12/2001 | C07D/495/04 |
| WO | WO 9854190 A1 | * | 12/1998 | C07D/495/04 |
| WO | WO 3011868 A1 | * | 2/2003 | C07D/495/04 |

* cited by examiner

Primary Examiner—Mark L. Berch
(74) Attorney, Agent, or Firm—Nixon & Vanderhye

(57) ABSTRACT

A compound of formula

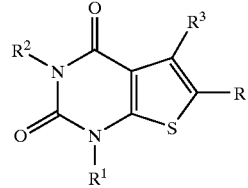

(I)

or a pharmaceutically acceptable salt thereof, wherein R is —C(O)Ar$^1$, —C(R$^4$)(R$^5$)Ar$^1$ or Ar$^3$; R$^3$ represents a group X—R$^{10}$ or Ar$^2$; X represents a bond or a group NR$^{11}$; and R$^{10}$ represents C$_{1-6}$ alkyl, C$_{2-6}$ alkenyl or C$_{2-6}$ alkynyl, each of which may be optionally substituted by one or more substituents independently selected from carboxyl, hydroxyl, —C(O)—R$^{12}$, C$_{3-6}$ cycloalkyl, morpholinyl, —NR$^{13}$R$^{14}$, —SR$^{15}$, —OR$^{16}$, phenyl and halophenyl, or R$^{10}$ represents a C$_{3-6}$ cycloalkylcarbonyl, —C(O)CH$_2$CN, halophenylcarbonyl or trifluoromethylcarbonyl group. The compounds or compositions thereof are useful in the treatment or prophylaxis of autoimmune, inflammatory, proliferative and hyperproliferative diseases.

11 Claims, No Drawings

COMPOUNDS

The present invention relates to thieno[2,3-d]pyrimidinediones, processes for their preparation, pharmaceutical compositions containing them and their use in therapy.

In accordance with the present invention, there is provided a compound of general formula

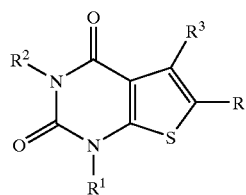

(I)

wherein:
R is —C(O)Ar$^1$, —C(R$^4$)(R$^5$)Ar$^1$ or Ar$^3$;
Ar$^1$ represents a 5- to 10-membered aromatic ring system wherein up to 3 ring atoms may be heteroatoms independently selected from nitrogen, oxygen and sulphur, the ring system being optionally substituted by one or more substituents independently selected from C$_{1-4}$ alkyl, C$_{1-4}$ alkoxy, halogen, trifluoromethyl, oxo, nitro, cyano, NR$^6$R$^7$ and —CH$_2$NR$^8$R$^9$;
R$^1$ and R$^2$ each independently represent a hydrogen atom, C$_{1-6}$ alkyl, C$_{3-6}$ alkenyl, CH$_2$C$_{3-5}$ cycloalkyl or C$_{3-6}$ cycloalkyl;
R$^3$ represents a group X—R$^{10}$ or Ar$^2$;
X represents a bond or a group NR$^{11}$;
Ar$^2$ represents a 5- or 6-membered aromatic ring wherein up to 4 ring atoms may be heteroatoms independently selected from nitrogen, oxygen and sulphur, the ring being optionally substituted by one or more substituents independently selected from C$_{1-4}$ alkyl, C$_{1-4}$ alkoxy, C$_{1-4}$ alkylthio, acetyl, halogen, trifluoromethyl, oxo, hydroxyl, amino (NH$_2$), nitro, cyano and benzyl;
R$^4$ represents a hydrogen atom or C$_{1-4}$ alkyl (e.g. methyl, ethyl, n-propyl or n-butyl);
R$^5$ represents a hydrogen atom or hydroxyl group;
R$^6$ and R$^7$ each independently represent a hydrogen atom or C$_{1-4}$ alkyl, or together with the nitrogen atom to which they are attached form a 5- to 7-membered saturated heterocyclic ring;
R$^8$ and R$^9$ each independently represent a hydrogen atom or C$_{1-4}$ alkyl, or together with the nitrogen atom to which they are attached form a 5- to 7-membered saturated heterocyclic ring;
R$^{10}$ represents C$_{1-6}$ alkyl, C$_{2-6}$ alkenyl or C$_{2-6}$ alkynyl, each of which may be optionally subsituted by one or more substituents independently selected from carboxyl, hydroxyl, —C(O)—R$^{12}$, C$_{3-6}$ cycloalkyl, morpholinyl, —NR$^{13}$R$^{14}$, —SR$^{15}$, —OR$^{16}$, phenyl and halophenyl, or
R$^{10}$ represents a C$_{3-6}$ cycloalkylcarbonyl, —C(O)CH$_2$CN, halophenylcarbonyl or trifluoromethylcarbonyl group;
R$^{11}$ represents a hydrogen atom or a C$_{1-6}$ alkyl group;
R$^{12}$ represents piperazinyl optionally substituted by a C$_{1-6}$ alkyl group, or
R$^{12}$ represents a group —NR$^{17}$R$^{18}$;
R$^{13}$ and R$^{14}$ each independently represent a hydrogen atom, or a C$_{1-4}$ alkyl, C$_{1-4}$ hydroxyalkyl or —C(O)—R$^{19}$ group, or
R$^{13}$ and R$^{14}$, together with the nitrogen atom to which they are attached, form a 5- to 7-membered saturated heterocyclic ring which may be optionally substituted by one or more substituents independently selected from C$_{1-4}$ alkyl, hydroxyl and oxo;
R$^{15}$ and R$^{16}$ each independently represent a 5- or 6-membered aromatic ring wherein up to 4 ring atoms may be heteroatoms independently selected from nitrogen, oxygen and sulphur, the ring being optionally substituted by one or more substituents independently selected from halogen atoms, cyano and C$_{1-4}$ alkyl;
R$^{17}$ and R$^{18}$ each independently represent a hydrogen atom, or a C$_{1-4}$ alkyl group optionally substituted by one or more substituents independently selected from halogen atoms and hydroxyl;
R$^{19}$ represents a C$_{1-6}$ alkyl or C$_{3-6}$ cycloalkyl group, each of which may be optionally substituted by a hydroxyl group; and
Ar$^3$ represents acenaphthenyl, indanyl or fluorenyl, each of which may be optionally substituted by one or more substituents independently selected from C$_{1-4}$ alkyl, C$_{1-4}$ alkoxy, halogen and trifluoromethyl;
or a pharmaceutically acceptable salt or solvate thereof.

In the present specification, unless otherwise indicated, an alkyl, alkenyl or alkynyl group or an alkyl, alkenyl or alkynyl moiety in a substituent group may be linear or branched. It will be appreciated that when R represents a group —C(R$^4$)(R$^5$)Ar$^1$, R$^5$ may represent a hydroxyl group only when Ar$^1$ is bonded to —C(R$^4$)(R$^5$) through a carbon atom and not a heteroatom. Furthermore, it should be understood that when R represents a group —C(O)Ar$^1$, Ar$^1$ is bonded through a carbon atom and not a heteroatom to the moiety —C(O). A halophenyl substituent group is a phenyl group substituted by up to 5 halogen atoms (e.g. fluorine, chlorine, bromine or iodine). If there are two or more halogen atoms, these may be the same or different. A hydroxyalkyl may contain more than one hydroxyl group but a single hydroxyl group is preferred. When R$^3$ represents X—R$^{10}$, X is a bond and R$^{10}$ represents C$_{2-6}$ alkenyl or C$_{2-6}$ alkynyl substituted by a hydroxyl or —NR$^{13}$R$^{14}$ group, the substituent will not be attached to an unsaturated carbon atom. When R$^3$ represents X—R$^{10}$, X is NR$^{11}$ and R$^{10}$ represents C$_{2-6}$ alkenyl or C$_{2-6}$ alkynyl substituted by a hydroxyl or —NR$^{13}$R$^{14}$ group, the substituent will not be attached to an unsaturated carbon atom, and nor is R$^{10}$ linked to X through an unsaturated carbon atom.

R preferably represents —C(R$^4$)(R$^5$)Ar$^1$. R$^4$ and R$^5$ preferably both represent a hydrogen atom.

Ar$^1$ represents a 5- to 10-membered aromatic ring system wherein up to 3 ring atoms may be heteroatoms independently selected from nitrogen, oxygen and sulphur, the ring system being optionally substituted by one or more (e.g. one, two, three or four) substituents independently selected from C$_{1-4}$ alkyl (e.g. methyl, ethyl, n-propyl or n-butyl), C$_{1-4}$ alkoxy (e.g. methoxy, ethoxy, n-propoxy or n-butoxy), halogen (e.g. fluorine, chlorine, bromine or iodine), trifluoromethyl, oxo, nitro, cyano, NR$^6$R$^7$ and —CH$_2$NR$^8$R$^9$. Preferred substituents to use are C$_{1-4}$ alkyl, halogen and, especially, trifluoromethyl.

The aromatic ring system may be monocyclic or polycyclic (e.g. bicyclic), examples of which include phenyl, naphthyl, pyrazolyl, thienyl, oxazolyl, imidazolyl, pyridinyl, pyridopyrrolyl, benzimidazolyl, indazolyl, benzothiazolyl, benzoxazolyl, thiazolyl and benzotriazolyl. Preferably, the aromatic ring system is monocyclic and 5- or 6-membered, especially phenyl.

R$^1$ and R$^2$ each independently represent a hydrogen atom, C$_{1-6}$, preferably C$_{1-4}$, alkyl (e.g. methyl, ethyl, n-propyl, 1-methylethyl, n-butyl, 2-methylpropyl, n-pentyl or n-hexyl), C$_{3-6}$, preferably C$_{3-4}$, alkenyl (e.g. 1-propenyl, 1-butenyl, 1-pentenyl or 1-hexenyl), $CH_2C_{3-5}$ cycloalkyl (cyclopropylmethyl, cyclobutylmethyl or cyclopentylmethyl) or $C_{3-6}$, preferably $C_{5-6}$, cycloalkyl (cyclopropyl, cyclobutyl, cyclopentyl or cyclohexyl).

Most preferably $R^1$ and $R^2$ each independently represent a $C_{1-4}$ alkyl group.

$R^6$ and $R^7$ each independently represent a hydrogen atom or $C_{1-4}$ alkyl (e.g. methyl, ethyl, n-propyl or n-butyl), or together with the nitrogen atom to which they are attached form a 5- to 7-membered saturated heterocyclic ring.

$R^8$ and $R^9$ each independently represent a hydrogen atom or $C_{1-4}$ alkyl (e.g. methyl, ethyl, n-propyl or n-butyl), or together with the nitrogen atom to which they are attached form a 5- to 7-membered saturated heterocyclic ring.

$Ar^2$ represents a 5- or 6-membered aromatic ring wherein up to 4 ring atoms may be heteroatoms independently selected from nitrogen, oxygen and sulphur, the ring being optionally substituted by one or more (e.g. one, two or three) substituents independently selected from $C_{1-4}$ alkyl (e.g. methyl, ethyl, n-propyl or n-butyl), $C_{1-4}$ alkoxy (e.g. methoxy, ethoxy, n-propoxy or n-butoxy), $C_{1-4}$ alkylthio (e.g. methylthio, ethylthio, n-propylthio or n-butylthio), acetyl, halogen (e.g. fluorine, chlorine, bromine or iodine), trifluoromethyl, oxo, hydroxyl, amino, nitro, cyano and benzyl. A preferred substituent is $C_{1-4}$ alkyl or acetyl. Examples of aromatic rings that can be used include phenyl, furyl, pyridyl, thienyl, pyrrolyl, thiazolyl, thiadiazolyl, oxazolyl, imidazolyl, triazolyl and tetrazolyl.

$R^{10}$ represents $C_{1-6}$, preferably $C_{1-4}$, alkyl, $C_{2-6}$, preferably $C_{2-5}$, alkenyl or $C_{2-6}$, preferably $C_{4-6}$, alkynyl, each of which may be optionally subsituted by one or more (e.g. one, two or three) substituents independently selected from carboxyl, hydroxyl, —C(O)—$R^{12}$, $C_{3-6}$ cycloalkyl, morpholinyl, —$NR^{13}R^{14}$, —$SR^{15}$, —$OR^{16}$, phenyl and halophenyl, or $R^{10}$ represents a $C_{3-6}$ cycloalkylcarbonyl, $C(O)CH_2CN$, halophenylcarbonyl or trifluoromethylcarbonyl group.

$R^{11}$ represents a hydrogen atom or a $C_{1-6}$, preferably $C_{1-4}$, alkyl, especially methyl, group.

$R^{12}$ represents piperazinyl optionally substituted by a $C_{1-6}$, preferably $C_{1-4}$, alkyl, especially methyl, group or a group —$NR^{17}R^{18}$.

$R^{13}$ and $R^{14}$ each independently represent a hydrogen atom or a $C_{1-4}$ alkyl (especially methyl), $C_{1-4}$ hydroxyalkyl (particularly hydroxymethyl or hydroxyethyl) or —C(O)—$R^{19}$ group, or $R^{13}$ and $R^{14}$, together with the nitrogen atom to which they are attached, form a 5- to 7-membered saturated heterocyclic ring which may be optionally substituted by one or more (e.g. one, two or three) substituents independently selected from $C_{1-4}$ alkyl (especially methyl), hydroxyl and oxo.

$R^{15}$ and $R^{16}$ each independently represent a 5- or 6-membered aromatic ring wherein up to 4 ring atoms may be heteroatoms independently selected from nitrogen, oxygen and sulphur, the ring being optionally substituted by one or more (e.g. one, two or three) substituents independently selected from halogen atoms (e.g. fluorine, chlorine, bromine or iodine), cyano and $C_{1-4}$ alkyl (especially methyl). Examples of aromatic rings that can be used include phenyl, furyl, pyridyl, thienyl, pyrrolyl, thiazolyl, thiadiazolyl, oxazolyl, imidazolyl, triazolyl and tetrazolyl.

$R^{17}$ and $R^{18}$ each independently represent a hydrogen atom, or a $C_{1-4}$ alkyl (e.g. methyl, ethyl, n-propyl or n-butyl) group optionally substituted by one or more (e.g. one, two or three) substituents independently selected from halogen atoms (e.g. fluorine, chlorine, bromine or iodine) and hydroxyl.

$R^{19}$ represents a $C_{1-6}$, preferably $C_{1-4}$, and especially $C_{1-2}$, alkyl or $C_{3-6}$, preferably $C_{3-5}$, and especially $C_3$ cycloalkyl group, each of which may be optionally substituted by a hydroxyl group.

$Ar^3$ represents acenaphthenyl, indanyl or fluorenyl, each of which may be optionally substituted by one or more (e.g. one, two or three) substituents independently selected from $C_{1-4}$ alkyl (e.g. methyl, ethyl, n-propyl or n-butyl), $C_{1-4}$ alkoxy (e.g. methoxy, ethoxy, n-propoxy or n-butoxy), halogen (e.g. fluorine, chlorine, bromine or iodine) and trifluoromethyl.

Preferred compounds of the invention include:

5-(3-Hydroxy-3-methyl-1-butynyl)-1-isobutyl-3-methyl-6-[2-(trifluoromethyl)benzyl]-thieno[2,3-d]pyrimidine-2,4(1H,3H)-dione, 3-Methyl-5-[3-(4-methyl-1-piperazinyl)-3-oxo-1-propenyl]-1-(2-methylpropyl)-6-[[2-(trifluoromethyl)phenyl]methyl]-thieno[2,3-d]pyrimidine-2,4(1H,3H)-dione, 3-[1,2,3,4-Tetrahydro-3-methyl-1-(2-methylpropyl)-2,4-dioxo-6-[[2-(trifluoromethyl)phenyl]methyl]-thieno[2,3-d]pyrimidin-5-yl]-2-propenoic acid, 5-[3-Hydroxy-3-methyl-1-butenyl]-3-methyl-1-(2-methylpropyl)-6-[[2-(trifluoromethyl)phenyl]methyl]-thieno[2,3-d]pyrimidine-2,4(1H,3H)-dione, (E) and (Z)-5-[2-cyclopentylethenyl]-3-methyl-1-(2-methylpropyl)-6-[[2-(trifluoromethyl)phenyl]methyl]-thieno[2,3-d]pyrimidine-2,4(1H,3H)-dione, 3-Methyl-1-(2-methylpropyl)-5-(3-thienyl)-6-[[2-(trifluoromethyl)phenyl]methyl]-thieno[2,3-d]pyrimidine-2,4(1H,3H)-dione, 5-(5-Acetyl-2-thienyl)-3-methyl-1-(2-methylpropyl)-6-[[2-(trifluoromethyl)phenyl]methyl]-thieno[2,3-d]pyrimidine-2,4(1H,3H)-dione, 5-(Hydroxymethyl)-3-methyl-1-(2-methylpropyl)-6-[[2-(trifluoromethyl)phenyl]methyl]-thieno[2,3-d]pyrimidine-2,4(1H,3H)-dione, 3-Methyl-1-(2-methylpropyl)-5-(4-morpholinylmethyl)-6-[[2-(trifluoromethyl)phenyl]methyl]-thieno[2,3-d]pyrimidine-2,4(1H,3H)-dione, 5-[(4-Hydroxy-3-methyl-1-piperidinyl)methyl]-3-methyl-1-(2-methylpropyl)-6-[[2-(trifluoromethyl)phenyl]methyl]-thieno[2,3-d]pyrimidine-2,4(1H,3H)-dione, 5-[[(2-Hydroxyethyl)methylamino]methyl]-3-methyl-1-(2-methylpropyl)-6-[[2-(trifluoromethyl)phenyl]methyl]-thieno[2,3-d]pyrimidine-2,4(1H,3H)-dione, 3-Methyl-5-[[(2-methyl-3-furanyl)thio]methyl]-1-(2-methylpropyl)-6-[[2-(trifluoromethyl)phenyl]methyl]-thieno[2,3-d]pyrimidine-2,4(1H,3H)-dione, 3-Methyl-1-(2-methylpropyl)-5-[(1,3,4-thiadiazol-2-ylthio)methyl]-6-[[2-(trifluoromethyl)phenyl]methyl]-thieno[2,3-d]pyrimidine-2,4(1H,3H)-dione, 3-Methyl-1-(2-methylpropyl)-5-[[(1-methyl-1H-tetrazol-5-yl)thio]methyl]-6-[[2-(trifluoromethyl)phenyl]methyl]-thieno[2,3-d]pyrimidine-2,4(1H,3H)-dione, 5-[[(3-Chlorophenyl)thio]methyl]-3-methyl-1-(2-methylpropyl)-6-[[2-(trifluoromethyl)phenyl]methyl]-thieno[2,3-d]pyrimidine-2,4(1H,3H)-dione, 3-[[1,2,3,4-Tetrahydro-3-methyl-1-(2-methylpropyl)-2,4-dioxo-6-[[2-(trifluoromethyl)phenyl]methyl]-thieno[2,3-d]pyrimidin-5-yl]methoxy]-benzonitrile, 1-(Cyclopropylmethyl)-3-methyl-5-(phenoxymethyl)-6-[[2-(trifluoromethyl)phenyl]methyl]-thieno[2,3-d]pyrimidine-2,4(1H,3H)-dione, 3-Methyl-1-(2-methylpropyl)-5-[(4-oxo-1-piperidinyl)
methyl]-6-[[2-(trifluoromethyl)phenyl]methyl]-thieno
[2,3-d]pyrimidine-2,4(1H,3H)-dione,
2-Hydroxy-N-[[1,2,3,4-tetrahydro-3-methyl-1-(2-
methylpropyl)-2,4-dioxo-6-[[2-(trifluoromethyl)
phenyl]methyl]-thieno[2,3-d]pyrimidin-5-yl]methyl]-
acetamide,
1-Hydroxy-N-[[1,2,3,4-tetrahydro-3-methyl-1-(2-
methylpropyl)-2,4-dioxo-6-[[2-(trifluoromethyl)
phenyl]methyl]-thieno[2,3-d]pyrimidin-5-yl]methyl]-
cyclopropanecarboxamide,
1,2,3,4-Tetrahydro-N-(2-hydroxyethyl)-N,3-dimethyl-1-
(2-methylpropyl)-2,4-dioxo-6-[[2-(trifluoromethyl)
phenyl]methyl]-thieno[2,3-d]pyrimidine-5-acetamide,
N-(2-Fluoroethyl)-1,2,3,4-tetrahydro-3-methyl-1-(2-
methylpropyl)-2,4-dioxo-6-[[2-(trifluoromethyl)
phenyl]methyl]-thieno[2,3-d]pyrimidine-5-acetamide,
1,2,3,4-Tetrahydro-3-methyl-1-(2-methylpropyl)-β,2,4-
trioxo-6-[[2-(trifluoromethyl)phenyl]methyl]-thieno[2,
3-d]pyrimidine-5-propanenitrile,
3-Methyl-1-(2-methylpropyl)-5-[(E)-2-phenylethenyl]-6-
[[2-(trifluoromethyl)phenyl]methyl]-thieno[2,3-d]
pyrimidine-2,4(1H,3H)-dione,
Cyclopropanecarboxamide, N-[1,2,3,4-tetrahydro-3-
methyl-1-(2-methylpropyl)-2,4-dioxo-6-[[2-
(trifluoromethyl)phenyl]methyl]thieno[2,3-d]
pyrimidin-5-yl],
2,2,2-Trifluoro-N-[1,2,3,4-tetrahydro-3-methyl-1-(2-
methylpropyl)-2,4-dioxo-6-[[2-(trifluoromethyl)
phenyl]methyl]thieno[2,3-d]pyrimidin-5-yl]-
acetamide,
5-(Dimethylamino)-3-methyl-1-(2-methylpropyl)-6-[[2-
(trifluoromethyl)phenyl]methyl]-thieno[2,3-d]
pyrimidine-2,4(1H,3H)-dione,
1,2,3,4-Tetrahydro-3-methyl-1-(2-methylpropyl)-2,4-
dioxo-6-[[2-(trifluoromethyl)phenyl]methyl]-thieno[2,
3-d]pyrimidine-5-propanoic acid,
5-(3-Hydroxypropyl)-3-methyl-1-(2-methylpropyl)-6-
[[2-(trifluoromethyl)phenyl]methyl]-thieno[2,3-d]
pyrimidine-2,4(1H,3H)-dione,
5-[(2-Fluorophenyl)hydroxymethyl]-3-methyl-1-(2-
methylpropyl)-6-[[2-(trifluoromethyl)phenyl]methyl]-
thieno[2,3-d]pyrimidine-2,4(1H,3H)-dione,
5-(2-Fluorobenzoyl)-3-methyl-1-(2-methylpropyl)-6-[[2-
(trifluoromethyl)phenyl]methyl]-thieno[2,3-d]
pyrimidine-2,4(1H,3H)-dione,
and their pharmaceutically acceptable salts and solvates.

The present invention further provides a process for the
preparation of a compound of formula (I) as defined above
which comprises,
(a) when $R^3$ represents $Ar^2$, reacting a compound of general
formula

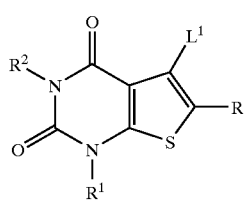

(II)

wherein $L^1$ represents a leaving group (e.g. a halogen atom
such as bromine) and R, $R^1$ and $R^2$ are defined as in formula (I), with a (hetero)aromatic boronic acid of general formula

(III)

wherein $Ar^2$ is defined as in formula (I), in the presence of
a palladium (0) species; or (b) when $R^3$ represents $X—R^{10}$, X represents a bond and $R^{10}$
represents a $C_{2-6}$ alkenyl or alkynyl group optionally
substituted as defined in formula (I), reacting a compound
of formula (II) as defined in (a) above with a compound
of general formula (IV), $R^{10'}—H$, wherein $R^{10'}$ represents
a $C_{2-6}$ alkenyl or alkynyl group optionally substituted as
defined in $R^{10}$ of formula (I) which comprises a terminal
carbon-carbon double or triple bond, in the presence of a
palladium (II) species and optionally either a copper (I)
species or a coordinating ligand (e.g. a triaryl phospine
ligand); or (c) when $R^3$ represents $X—R^{10}$, X represents a bond and $R^{10}$
represents a $C_{1-6}$ alkyl group optionally substituted as
defined in formula (I), reacting a corresponding com-
pound of formula (I) in which $R^{10}$ represents a $C_{2-6}$
alkenyl or alkynyl group optionally substituted as defined
in formula (I) with hydrogen in the presence of a palla-
dium or platinum catalyst; or (d) when $R^3$ represents $X—R^{10}$, X represents a bond and $R^{10}$
represents a $C_{2-6}$ alkenyl or alkynyl group optionally
substituted as defined in formula (I), oxidising a com-
pound of formula (I) as described in (c) above; or (e) when $R^3$ represents $X—R^{10}$, X represents a bond and $R^{10}$
represents a $C_{3-6}$ cycloalkylcarbonyl, $—C(O)CH_2CN$,
halophenylcarbonyl or trifluoromethylcarbonyl group,
reacting a compound of formula (II) as defined in (a)
above, with a suitable Grignard reagent (e.g. ethyl mag-
nesium bromide) and then with a compound of general
formula (V), $R^{10''}—H$, wherein $R^{10''}$ represents a $C_{3-6}$
cycloalkylcarbonyl, $—C(O)CH_2CN$, halophenylcarbonyl
or trifluoromethylcarbonyl group, followed by an oxida-
tion reaction (e.g. using oxalyl chloride and
dimethylsulphoxide); or (f) when $R^3$ represents $X—R^{10}$ and X represents a group
$NR^{11}$, reacting a compound of general formula

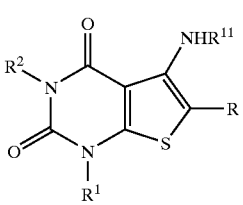

(VI)

wherein R, $R^1$, $R^2$ and $R^{11}$ are as defined in formula (I), with
a compound of general formula (VII), $R^{10}-L^2$, wherein $L^2$
represents a leaving group and $R^{10}$ is as defined in formula
(I); or (g) when $R^3$ represents $X—R^{10}$, X represents a bond and $R^{10}$
represents $CH_2CO_2H$, reacting a compound of general
formula

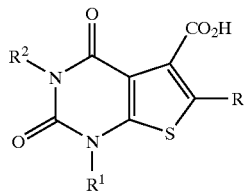

(VIII)

wherein R, $R^1$ and $R^2$ are as defined in formula (I), with an activating agent (e.g. oxalyl chloride) followed by diazomethane, and causing the resulting intermediate to undergo a Wolff rearrangement in the presence of a metal oxide catalyst to obtain a compound of formula (I);
and optionally after (a), (b), (c), (d), (e), (f) or (g) converting the compound of formula (I) obtained to a further compound of formula (I) and/or forming a pharmaceutically acceptable salt or solvate of the compound of formula (I).

Process (a) is conveniently carried out in an inert, aprotic solvent such as glyme (1,2-dimethoxyethane) at a temperature in the range from −20° C. to 120° C., preferably from 50° C. to 100° C.

Process (b) is conveniently carried out in an inert, aprotic solvent such as acetonitrile at a temperature in the range from −20° C. to 100° C., preferably from 50° C. to 100° C. If the compound of formula (IV) is an alkene, the palladium (II) species is used with a coordinating ligand whereas if the compound of formula (IV) is an alkyne, then the palladium (II) species is used with a copper (I) species. Examples of suitable sources of the palladium and copper species include $Pd(PPh_3)_2Cl_2$ and CuI.

Process (c) may be carried out in an alcoholic solvent such as ethanol at a temperature in the range from 10° C. to 50° C., preferably from 20° C. to 30° C., in the presence of a catalyst (e.g. Pd—C) under an atmosphere of hydrogen at a pressure of 1 to 5 bar.

Any suitable oxidant may be used in process (d).

In process (e), reaction with the Grignard reagent may be performed in an inert, aprotic solvent such as tetrahydrofuran at a temperature in the range from −20° C. to 50° C., preferably from 0° C. to 25° C. Subsequent reaction with the compound of general formula (V) is conveniently carried out in the same solvent at a temperature in the range from −20° C. to 100° C., preferably from 0° C. to 25° C. The oxidation step may be performed in an inert solvent (e.g. dichloromethane) with oxalyl chloride and dimethylsulphoxide at a temperature in the range from 0° C. to 50° C., preferably from 15° C. to 20° C.

Process (f) is conveniently carried out in an inert, aprotic solvent such as tetrahydrofuran at a temperature in the range from −20° C. to 100° C., preferably from 0° C. to 25° C.

Process (g) may be carried out with a chlorinating agent (e.g. oxalyl chloride) in an inert solvent (e.g. dichloromethane) at a temperature in the range from 0° C. to 50° C., preferably from 15° C. to 20° C., followed by treatment of the activated acid with diazomethane or, preferably, trimethylsilyldiazomethane in an inert solvent (e.g. dichloromethane) at a temperature in the range from 0° C. to 50° C., preferably from 15° C. to 20° C. The adduct may then be heated in a $C_{1-8}$ alcohol (preferably methanol) at a temperature of 50° C. to 100° C., in the presence of a catalyst (preferably silver oxide), followed by heating at reflux in an alcoholic solvent (preferably ethanol) containing aqueous mineral acid (preferably HCl).

Compounds of formulae (II) to (VIII) are either commercially available, are well known in the literature or may be prepared easily using known techniques. Compounds of formula (I) (e.g. acids) can be converted to farther compounds of formula (I) (e.g. alcohols, which in turn can be converted to aldehydes and ketones) according to known techniques.

It will be appreciated by those skilled in the art that in the processes of the present invention certain functional groups such as hydroxyl or amino groups in the starting reagents or intermediate compounds may need to be protected by protecting groups. Thus, the preparation of the compounds of formula (I) may involve, at an appropriate stage, the removal of one or more protecting groups.

The protection and deprotection of functional groups is fully described in 'Protective Groups in Organic Chemistry', edited by J. W. F. McOmie, Plenum Press (1973), and 'Protective Groups in Organic Synthesis', 2nd edition, T. W. Greene & P. G. M. Wuts, Wiley-Interscience (1991).

The compounds of formula (I) above may be converted to a pharmaceutically acceptable salt or solvate thereof, preferably an acid addition salt such as a hydrochloride, hydrobromide, phosphate, acetate, fumarate, maleate, tartrate, citrate, oxalate, methanesulfonate or p-toluenesulfonate, or an alkali metal salt such as a sodium or potassium salt.

Certain compounds of formula (I) are capable of existing in stereoisomeric forms. It will be understood that the invention encompasses all geometric and optical isomers of the compounds of formula (I) and mixtures thereof including racemates. Tautomers and mixtures thereof also form an aspect of the present invention.

Isomers may be resolved or separated by conventional techniques, e.g. chromatography or fractional crystallisation. Enantiomers may be isolated by separation of a racemic or other mixture of the compounds using conventional techniques (e.g. chiral High Performance Liquid Chromatography (HPLC)). Alternatively the desired optical isomers may be made by reaction of the appropriate optically active starting materials under conditions which will not cause racemisation, or by derivatisation, for example with a homochiral acid followed by separation of the diastereomeric derivatives by conventional means (e.g. HPLC, chromatography over silica) or may be made with achiral starting materials and chiral reagents. All stereoisomers are included within the scope of the invention.

The compounds of the invention may be isolated from their reaction mixtures using conventional techniques.

The compounds of the invention are useful because they possess pharmacological activity in human and non-human animals. They are therefore indicated as pharmaceuticals for use in the (prophylactic) treatment of autoimmune, inflammatory, proliferative and hyperproliferative diseases and immunologically-mediated diseases including rejection of transplanted organs or tissues and Acquired Immunodeficiency Syndrome (AIDS).

Examples of these conditions are:

(1) (the respiratory tract) airways diseases including chronic obstructive pulmonary disease (COPD); asthma, such as bronchial, allergic, intrinsic, extrinsic and dust asthma, particularly chronic or inveterate asthma (e.g. late asthma and airways hyper-responsiveness); bronchitis; acute, allergic, atrophic rhinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis; seasonal rhinitis including rhinitis nervosa (hay fever) and vasomotor rhinitis; sarcoidosis, farmer's lung and related diseases, fibroid lung and idiopathic interstitial pneumonia;

(2) (bone and joints) rheumatoid arthritis, seronegative spondyloarthropathies (including ankylosing spondylitis, psoriatic arthritis and Reiter's disease), Behcet's disease, Sjogren's syndrome and systemic sclerosis;
(3) (skin) psoriasis, atopical dermatitis, contact dermatitis and other eczmatous dermitides, seborrhoetic dermatitis, Lichen planus, Pemphigus, bullous Pemphigus, Epidermolysis bullosa, urticaria, angiodermas, vasculitides, erythemas, cutaneous eosinophilias, uveitis, Alopecia areata and vernal conjunctivitis;
(4) (gastrointestinal tract) Coeliac disease, proctitis, eosinopilic gastro-enteritis, mastocytosis, Crohn's disease, ulcerative colitis, food-related allergies which have effects remote from the gut, e.g., migraine, rhinitis and eczema;
(5) (other tissues and systemic disease) multiple sclerosis, atherosclerosis, Acquired Immnunodeficiency Syndrome (AIDS), lupus erythematosus, systemic lupus, erythematosus, Hashimoto's thyroiditis, myasthenia gravis, type I diabetes, nephrotic syndrome, eosinophilia fascitis, hyper IgE syndrome, lepromatous leprosy, sezary syndrome and idiopathic thrombocytopenia pupura;
(6) (allograft rejection) acute and chronic following, for example, transplantation of kidney, heart, liver, lung, bone marrow, skin and cornea; and chronic graft versus host disease; and
(7) cancer.

Accordingly, the present invention provides a compound of formula (I) or a pharmaceutically acceptable salt or solvate thereof as hereinbefore defined for use in therapy.

In another aspect, the invention provides the use of a compound of formula (I) or a pharmaceutically acceptable salt or solvate thereof as hereinbefore defined in the manufacture of a medicament for use in therapy.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

The invention further provides a method of effecting immunosuppression (e.g. in the treatment of allograft rejection) which comprises administering to a patient a therapeutically effective amount of a compound of formula (I) or a pharmaceutically acceptable salt or solvate thereof as hereinbefore defined.

The invention still further provides a method of treating, or reducing the risk of, an airways disease (e.g. asthma or COPD) in a patient suffering from, or at risk of, said disease, which comprises administering to the patient a therapeutically effective amount of a compound of formula (I) or a pharmaceutically acceptable salt or solvate thereof as hereinbefore defined.

For the above-mentioned therapeutic uses the dosage administered will, of course, vary with the compound employed, the mode of administration, the treatment desired and the disorder indicated. However, in general, for effecting immunosuppression, the daily dosage of the compound of formula (I) will be in the range from 0.1 mg/kg, preferably from 0.3 mg/kg, more preferably from 0.5 mg/kg and still more preferably from 1 mg/kg up to and including 30 mg/kg. For the treatment of airways diseases, the daily dosage of the compound of formula (I) will typically be in the range from 0.001 mg/kg to 30 mg/kg.

The compounds of formula (I) and pharmaceutically acceptable salts and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99% w (per cent by weight), more preferably less than 80% w, e.g. from 0.10 to 70% w, and even more preferably less than 50% w, of active ingredient, all percentages by weight being based on total composition.

Thus, the present invention also provides a pharmaceutical composition comprising a compound of formula (I) or a pharmaceutically acceptable salt or solvate thereof as hereinbefore defined, in association with a pharmaceutically acceptable adjuvant, diluent or carrier.

The invention further provides a process for the preparation of a pharmaceutical composition of the invention which comprises mixing a compound of formula (I) or a pharmaceutically acceptable salt or solvate thereof as hereinbefore defined, with a pharmaceutically acceptable adjuvant, diluent or carrier.

The pharmaceutical composition of the invention may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally.

The invention will now be further explained by reference to the following illustrative examples.

EXAMPLE 1

5-(3-Hydroxy-3-methyl-1-butynyl)-1-isobutyl-3-methyl-6-[2-(trifluoromethyl)benzyl]-thieno[2,3-d]pyrimidine-2,4(1H,3H)-dione

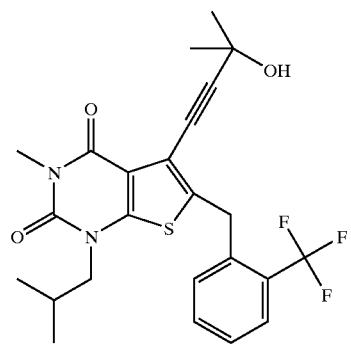

a) 6-Bromo-3-methyl-1-(2-methylpropyl)-thieno[2,3-d]pyrimidine-2,4(1H,3H)-dione

Bromine (2.79 ml) in dry dichloromethane (25 ml) was added dropwise to a solution of 3-methyl-1-(2-methylpropyl)-thieno[2,3-d]pyrimidine-2,4(1H,3H)-dione (12.0 g, WO 98/54190) in dry dichloromethane (100 ml) and stirred at room temperature for 30 minutes. The solution was concentrated under reduced pressure. The residue was dissolved in ethyl acetate and washed with sodium metabisulfite solution. The organic layer was dried over anhydrous magnesium sulfate, filtered and concentrated under reduced pressure to give the sub-title compound as a cream solid. (15.85 g)

MS (APCI) 318 [M+H]+ b) 5-Bromo-6-[hydroxy[2-(trifluoromethyl)phenyl]methyl]-3-methyl-1-(2-methylpropyl)-thieno[2,3-d]pyrimidine-2,4(1H,3H)-dione Lithium diisopropylamide (2.0M, 14.26 ml) was added dropwise to a solution of 6-bromo-3-methyl-1-(2-methylpropyl)-thieno[2,3-d]pyrimidine-2,4(1H,3H)-dione (8.22 g) in dry tetrahydrofuran (200 ml) at −78° C. After 15 minutes, a solution of o-trifluoromethyl benzaldehyde (3.76 ml) in dry tetrahydrofuran (20 ml) was added and the reaction was stirred for 3 hours at −78° C. The reaction mixture was poured into saturated ammonium chloride solution and allowed to warm to room temperature. The mixture was extracted with ethyl acetate and the combined extracts were washed with water, dried over anhydrous magnesium sulfate, filtered and concentrated under reduced pressure. The residue was triturated with 15% ethyl acetate in isohexane and the solid filtered off and dried under vacuum to give the sub-title compound as a cream solid (7.59 g).

MS (APCI) 490.0[M+H]+ c) 5-Bromo-1-isobutyl-3-methyl-6-[2-(trifluoromethyl)benzyl]-thieno[2,3-d]pyrimidine-2,4(1H,3H)-dione 5-Bromo-6-{hydroxy[2-(trifluoromethyl)phenyl]methyl}-1-isobutyl-3-methyl-thieno[2,3-d]pyrimidine-2,4(1H,3H)-dione (33.47 g) was dissolved in triethyl silane (100 mls) and cooled to 0° C. before trifluoroacetic acid (100 mls) was added dropwise. After complete addition the resultant thick suspension was diluted by the addition of DCM (100 mls) and the reaction was stirred at room temperature for 18 hours. The reaction mixture was then concentrated in vacuo and partitioned between DCM and 50% aqueous sodium hydrogen carbonate. The organic layer was collected, dried over magnesium sulfate, filtered and concentrated in vacuo. The resultant off white solid was stirred vigorously with isohexane for 1 hour before being collected by filtration to yield 27.286 g (84.5%) of the subtitle compound.

MS: [M+H]+ 476 d) 5-(3-Hydroxy-3-methyl-1-butynyl)-1-isobutyl-3-methyl-6-[2-(trifluoromethyl)benzyl]-thieno[2,3-d]pyrimidine-2,4(1H,3H)-dione Copper (I) iodide (5 mg) was added to a stirred solution of 6-bromo-3-methyl-1-(2-methylpropyl)-thieno[2,3-d]pyrimidine-2,4(1H,3H)-dione in a mixture of acetonitrile (2 ml), triethylamine (2 ml), dichloro(bistriphenylphosphine)palladium(II) (37 mg) and 2-methyl-3-butyn-2-ol (0.07 ml). The reaction mixture was heated at 95° C. for 24 hours. The mixture was cooled to room temperature, and filtered (hyflo). The filtrate was concentrated in vacuo and purified by biotage eluting with 1:1 v/v ethyl acetate:hexane to afford the subtitle compound as a pale orange solid.

MS: [M+H]+ 479

EXAMPLE 2

3-Methyl-5-[3-(4-methyl-1-piperazinyl)-3-oxo-1-propenyl]-1-(2-methylpropyl)-6-[[2-(trifluoromethyl)phenyl]methyl]-thieno[2,3-d]pyrimidine-2,4(1H,3H)-dione

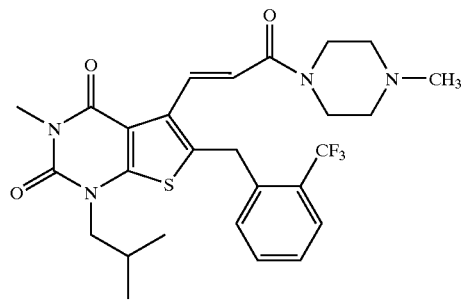

Acryloyl chloride (0.65 ml) was added dropwise to a solution of 1-methylpiperazine (0.94 ml) and triethylamine (2 ml) in acetonitrile (10 ml) in a pressure tube at 0° C. and stirred at room temperature for 1 hour. 5-Bromo-3-methyl-1-(2-methylpropyl)-6-[[2-(trifluoromethyl)phenyl]methyl]-thieno[2,3-d]pyrimidine-2,4(1H,3H)-dione (0.40 g, Example 1c)), palladium acetate (0.019 g) and tri-o-tolylphosphine (0.051 g) was added to the pressure tube and the reaction was heated at 70° C. for 21 hours. After cooling, the reaction mixture was concentrated under reduced pressure. The residue was purified by flash silica chromatography eluting with a gradient of 0–5% ethanol in dichloromethane to give a brown solid. The solid was triturated with acetonitrile to give the title compound as a white powder (0.042 g).

MS(ES+) 549[M+H]+

1HNMR(CDCl3) δ 0.95(6H,d); 2.21(1H,septet); 2.26(3H,s); 2.29–2.39(4H,m); 3.42(3H,s); 3.42–3.43(2H,m); 3.72–3.74(2H,m); 3.73(2H,s); 4.41(2H,s); 6.85(1H,d); 7.18(1H;d); 7.38(1H,t); 7.49(1H,t); 7.70(1H,d); 7.92(1H,d).

EXAMPLE 3

3-[1,2,3,4-Tetrahydro-3-methyl-1-(2-methylpropyl)-2,4-dioxo-6-[[2-(trifluoromethyl)phenyl]methyl]-thieno[2,3-d]pyrimidin-5-yl]-2-propenoic acid

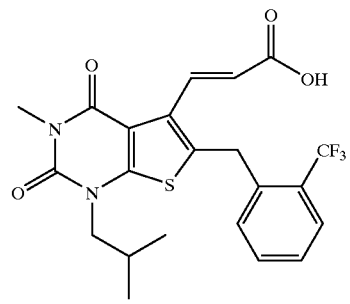

a) 3-[1,2,3,4-Tetrahydro-3-methyl-1-(2-methylpropyl)-2,4-dioxo-6-[[2-(trifluoromethyl)phenyl]methyl]-thieno[2,3-d]pyrimidin-5-yl]-2-propenoic acid, methyl ester 5-Bromo-3-methyl-1-(2-methylpropyl)-6-[[2-(trifluoromethyl)phenyl]methyl]-thieno[2,3-d]pyrimidine-2,4(1H,3H)-dione, (1.0 g, Example 1 part c)), methyl acrylate (0.95 ml), tri-o-tolylphosphine (0.128 g), palladium acetate (0.047 g) and triethylamine (4 ml) in acetonitrile (20 ml) were stirred in a pressure tube at 70° C. for 16 hours. After cooling, the reaction mixture was concentrated under reduced pressure. The residue was concentrated under reduced pressure and purified by flash silica chromatography eluting with a gradient of 0–1% ethanol in dichloromethane to give the sub-title compound as a brown foam (0.90 g).

MS(ES$^+$) 481[M+H]$^+$ $^1$HNMR (CDCl$_3$) δ 0.97(6H,d); 2.23(1H,septet); 3.42(3H, s); 3.68(2H,d); 3.79(3H,s); 4.40(2H,s); 6.16(1H,d); 7.19(1H, d); 7.40(1H,r); 7.50(1H,t); 7.72(1H,d); 8.24(1H,d)

b) 3-[1,2,3,4-Tetrahydro-3-methyl-1-(2-methylpropyl)-2,4-dioxo-6-[[2-(trifluoromethyl)phenyl]methyl]thieno[2,3-d]pyrimidin-5-yl]-2-propenoic acid Lithium hydroxide monohydrate (0.20 g) and water (6 ml) were added to a solution of 3-[1,2,3,4-tetrahydro-3-methyl-1-(2-methylpropyl)-2,4-dioxo-6-[[2-(trifluoromethyl)phenyl]methyl]-thieno[2,3-d]pyrimidin-5-yl]-2-propenoic acid, methyl ester (0.20 g) in tetrahydrofuran (7 ml) and stirred at room temperature for 20 hours. The solution was neutralised to pH7 and extracted with dichloromethane. The organic extracts were dried over anhydrous magnesium sulfate, filtered and concentrated in vacuo. The residue was purified by flash silica chromatography eluting with a gradient of 0–5% ethanol in dichloromethane to give the title compound as a white solid (0.10 g).

MS(ES$^+$) 467[M+H]$^+$ $^1$HNMR(CDCl$_3$) δ 0.94(6H,d); 2.17–2.27(1H,m); 3.42 (3H,s); 3.71(2H,d); 4.42(2H,s); 6.16(1H,d); 7.24(1H,d); 7.41(1H,t); 7.51(1H,t); 7.72(1H,d); 8.36(1H,d).

Using the method of Example 3 part a) the following compounds were prepared:

EXAMPLE 4

5-[3-Hydroxy-3-methyl-1-butenyl]-3-methyl-1-(2-methylpropyl)-6-[[2-(trifluoromethyl)phenyl]methyl]-thieno[2,3-d]pyrimidine-2,4(1H,3H)-dione

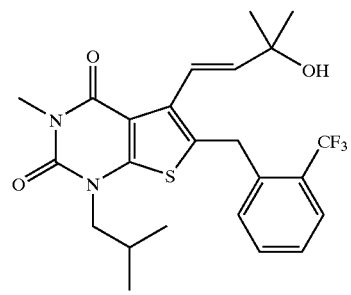

Prepared using 5-bromo-3-methyl-1-(2-methylpropyl)-6-[[2-(trifluoromethyl)phenyl]methyl]-thieno[2,3-d]pyrimidine-2,4(1H,3H)-dione and 2-methyl-3-buten-2-ol. The crude product was purified by flash silica chromatography eluting with a gradient of 0–2% ethanol in dichloromethane to give the title compound as a cream foam (0.20 g).

MS(APCI) 463[M–H$_2$O]$^+$ $^1$HNMR(CDCl$_3$) δ 0.98(6H,d); 1.36(6H,d); 2.22–2.31 (1H,m); 3.41(3H,s); 3.72(2H,d); 4.38(2H,s); 5.88(1H,d); 7.04(1H,d); 7.21(1H,d); 7.37(1H,t); 7.48(1H,t); 7.69(1H,d).

EXAMPLE 5

(E) and (Z)-5-[2-cyclopentylethenyl]-3-methyl-1-(2-methylpropyl)-6-[[2-(trifluoromethyl)phenyl]methyl]-thieno[2,3-d]pyrimidine-2,4(1H,3H)-dione

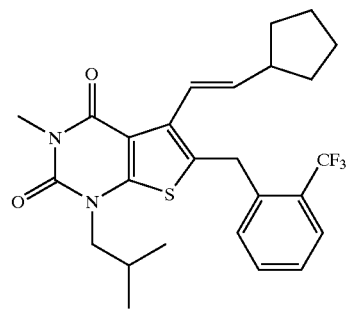

Prepared using 5-bromo-3-methyl-1-(2-methylpropyl)-6-[[2-(trifluoromethyl)phenyl]methyl]-thieno[2,3-d]pyrimidine-2,4(1H,3H)-dione and cyclopentyl-ethene. The crude product was purified by flash silica chromatography eluting with a gradient of 5–20% ethanol in dichloromethane to give the title compound as a yellow oil (0.17 g).

MS(APCI) 491[M+H]$^+$ $^1$HNMR(CDCl$_3$) δ 0.94(6H,d); 1.56–1.65(2H,m); 1.84 (1H,quintet); 1.84–1.89(1H,m); 2.17–2.33(4H,m); 2.86–2.94(1H,m); 3.01–3.06(1H,m); 3.40+3.42(3H,s); 4.25 (2H,d); 4.38+4.26(2H,2xs,); 5.32+5.37(1H,2xs); 5.65–5.72 (1H,m); 7.20(1H,d); 7.36(1H,t); 7.45–7.49(1H,m); 7.69(1H, d).

EXAMPLE 6

3-Methyl-1-(2-methylpropyl)-5-(3-thienyl)-6-[[2-(trifluoromethyl)phenyl]methyl]-thieno[2,3-d]pyrimidine-2,4(1H,3H)-dione

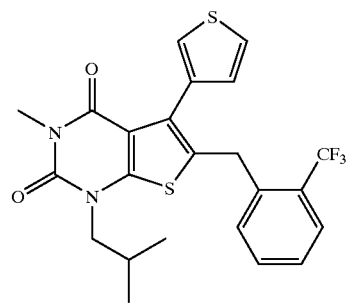

5-Bromo-3-methyl-1-(2-methylpropyl)-6-[[2-(trifluoromethyl)phenyl]methyl]-thieno[2,3-d]pyrimidine-2,4(1H,3H)-dione, (0.35 g, Example 1c)), thiophene-3-boronic acid (0.053 g), barium hydroxide octahydrate (0.15 g) and tetrakis(triphenylphosphine)palladium (0) (0.0097 g) in ethylene glycol dimethyl ether (6 ml) and water (1 ml) were combined in a sealed vial and stirred with heating at 80° C. for 18 hours. After cooling, the reaction mixture was absorbed onto silica and purified by flash silica chromatography eluting with 25% ethyl acetate in isohexane to give an oil. The oil was triturated with isohexane, filtered and dried under vacuum to give the title compound as a beige solid (0.020 g).

m.p. 113–114° C.

MS(APCI) 479[M+H]+

¹H NMR (CDCl₃) δ 0.97 (d, J=7.7 Hz, 6H), 2.30 (septet, J=7.7 Hz, 1H), 3.36 (s, 3H), 3.76 (d, J=7.7 Hz, 2H), 4.21 (s, 2H), 7.13 (dd, J=1.7, 5.4 Hz, 1H), 7.20 (dd, J=1.3, 2.9 Hz, 1H), 7.39 (dd, J=3.1, 5.0 Hz, 1H), 7.48 (t, J=7.7 Hz, 1H), 7.67 (d, J=7.5 Hz, 1H),

EXAMPLE 7

5-(5-Acetyl-2-thienyl)-3-methyl-1-(2-methylpropyl)-6-[[2-trifluoromethyl)phenyl]methyl]-thieno[2,3-d]pyrimidine-2,4(1H,3H)-dione

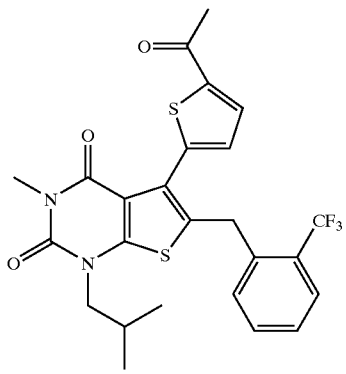

5-Bromo-3-methyl-1-(2-methylpropyl)-6-[[2-(trifluoromethyl)phenyl]methyl]-thieno[2,3-d]pyrimidine-2,4(1H,3H)-dione and 5-acetylthiophene-2-boronic acid were reacted by the method of Example 5. The crude product was purified by flash silica chromatography eluting with a gradient of 10–50% ethyl acetate in isohexane to give the title compound as an amber solid (0.054 g).

MS(APCI) 521[M+H]+

¹HNMR(CDCl₃) δ 0.97(6H,d); 2.27(1H,septet); 2.57(3H, s); 3.36(3H,s); 3.74(2H,d); 4.34(2H,s); 7.07(1H,d); 7.22–7.31(1H,m); 7.38(1H,t); 7.50(1H,t); 7.61(1H,d); 7.69 (1H,d).

EXAMPLE 8

5-(Hydroxymethyl)-3-methyl-1-(2-methylpropyl)-6-[[2-(trifluoromethyl)phenyl]methyl]-thieno[2,3-d]pyrimidine-2,4(1H,3H)-dione

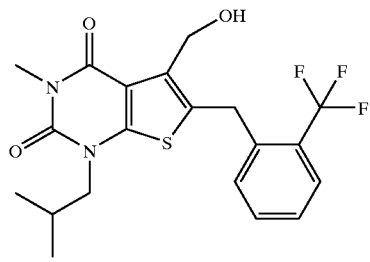

a) 1,2,3,4-Tetrahydro-3-methyl-1-(2-methylpropyl)-2,4-dioxo-6-[[2-(trifluoramethyl)phenyl]methyl]-thieno[2,3-d]prymidine-5-carboxylic acid, ethyl ester 5-Bromo-1-isobutyl-3-methyl-6-[2-(trifluoromethyl)benzyl]thieno[2,3-d]pyrimidine-2,4(1H,3H)-dione (3.6 g, Example 1c)) was dissolved in tetrahydrofuran (150 ml) at room temperature under an atmosphere of nitrogen. To this solution was added isobutyl magnesium bromide (4.9 mls, 2M in tetrahydrofuran). After 30 mins carbon dioxide gas was passed through the reaction and stirred for 2 hrs. The reaction mixture was then concentrated in vacuo and redissolved in ethanol (100 ml). Concentrated HCl (1 ml) was added and the reaction was heated at reflux for 36 hrs. The reaction was then concentrated in vacuo and partitioned between ethyl acetate and water. The organic layer was collected, dried over magnesium sulfate, filtered and evaporated to dryness in vacuo. The resultant gum was purified via chromatography eluting with 3:2 isohexane/diethyl ether to yield the sub title compound as a brown oil (2.3 g)

MS: [M+H]+=469 b) 5-(Hydroxymethyl)-3-methyl-1-(2-methylpropyl)-6-[[2-(trifluoromethyl)phenyl]methyl]-thieno[2,3-d]pyrimidine-2,4(1H3H)-dione The product of step a) (3.64 g) was dissolved in dry tetrahydrofuran (100 mls) to which LiAlH(OʹBu)₃ (22 mls, 1M in tetrahydrofuran) was added. The reaction was heated at 55° C. for 18 hrs before being quenched with water. The mixture was concentrated in vacuo and partitioned between ethyl acetate arid dilute HCl. The organics were collected and dried over magnesium sulfate, filtered, concentrated in vacua to yield a white solid. This solid was ultrasonicated with hexane for 1 hr before being collected via filtration to give the title compound (2.218 g)

MS: [M+H]+ 427

¹H NMR (DMSO d-6) δ 0.80 (6H, d), 1.88–1.96(1H, m), 2.89 (3H, s), 3.32 (2H, d), 4.56 (2H, s), 4.62 (2H,s), 7.36(1H, d), 7.48(1H, t), 7.64 (1H, t), 7.73(1H, d).

EXAMPLE 9

3-Methyl-1-(2-methylpropyl)-5-(4-morpholinylmethyl)-6-[[2-(trifluoromethyl)phenyl]methyl]-thieno[2,3-d]pyrimidine-2,4(1H,3H)-dione

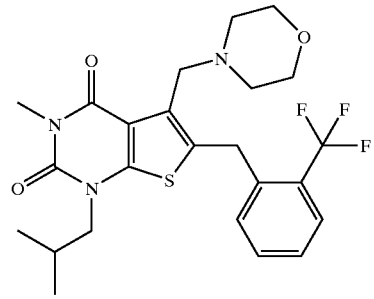

The product of Example 8 (100 mg) in DCM (3 mls) and thionyl chloride (54 ul) was stirred for 1 hr under an atmosphere of nitrogen. The mixture was then concentrated in vacuo and stored under a high vacuum for 4 hrs. The resultant residue was redissolved in DCM (1 ml) to which morpholine (260 ul) was added. The reaction was stirred for 18 hrs at room temperature. Water (2 ml) was then added to the reaction and the organics were then collected, concentrated in vacuo and purified via chromatography eluting with 0 to 10% methanol in DCM to yield the title compound (59 mg).

MS: [M+H]+=496

¹H NMR (DMSO d-6) δ 0.85 (6H, d), 2.08–2.16(1H, m), 2.33 (4H,m), 3.24 (3H, s), 3.43 (4H, m), 3.66 (2H, d), 3.86 (2H, s), 4.42 (2H,s), 7.45(1H, d), 7.48(1H, t), 7.63 (1H, t), 7.75(1H, d).

Using the method of Example 9, the following compounds were prepared:

EXAMPLE 10

5-[(4-Hydroxy-3-methyl-1-piperidinyl)methyl]-3-methyl-1-(2-methylpropyl)-6-[[2-(trifluoromethyl)phenyl]methyl]-thieno[2,3-d]pyrimidine-2,4(1H,3H)-dione

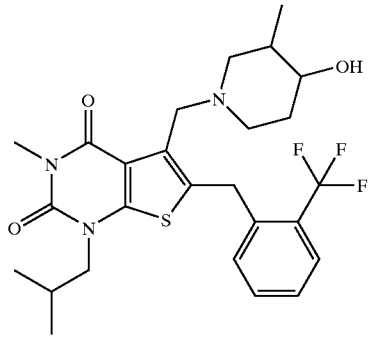

Prepared using 3-methyl-4-piperidinol.

MS: [M+H]$^+$=524

$^1$H NMR (DMSO d-6) δ 0.80 (3H, d), 0.86(6H,d), 1.24 (2H, m), 1.69(2H,m), 2.02(1H, t), 2.12(1H, m), 2.71 (2H, m), 2.88 (1H, m), 3.24(3H, s), 3.67 (2H, d), 3.82 (2H, s), 4.43(2H, s), 4.45(1H, d), 7.48(2H, m), 7.63(1H, t), 7.75(1H, d).

EXAMPLE 11

5-[[(2-Hydroxyethyl)methylamino]methyl]-3-methyl-1-(2-methylpropyl)-6-[[2-(trifluoromethyl)phenyl]methyl]-thieno[2,3-d]pyrimidine-2,4(1H,3H)-dione

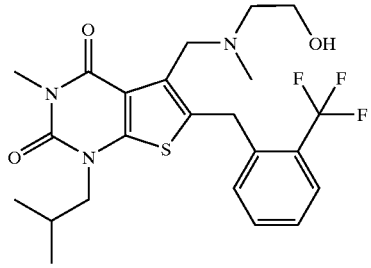

Prepared using 2-(methylamino)-ethanol

MS: [M+H]$^+$=484

$^1$H NMR (DMSO d-6) δ 0.86(6H,d), 2.11(1H, m), 2.16 (3H, s), 3.24(3H, s), 3.48 (2H, m), 3.66 (2H, d), 3.87(2H, s), 4.30(1H, t), 4.42(2H, s), 7.44(1H, d), (1H, t), 7.63(1H, t), 7.75(1H, d).

EXAMPLE 12

3-Methyl-5-[[(2-methyl-3-furanyl)thio]methyl]-1-(2-methylpropyl)-6-[[2-(trifluoromethyl)phenyl]methyl]-thieno[2,3-d]pyrimidine-2,4(1H,3H)-dione

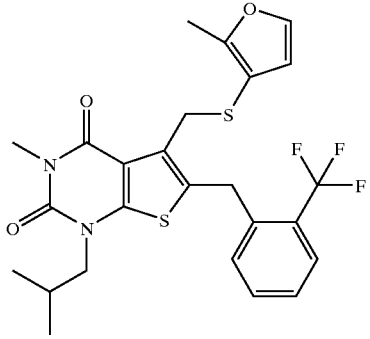

The product of Example 8 (100 mg) in dichloromethane (3 mls) and thionyl chloride (54 ul) was stirred for 1 hr under an atmosphere of nitrogen. The mixture was then concentrated in vacuo and stored under a high vacuum for 4 hrs. The resultant residue was redissolved in dichloromethane (1 ml) to which a solution of 3-furanthiol, 2-methyl-(2 mls, 0.1M in tetrahydrofuran), NaOH (1 ml, 0.2M in water) and triethylamine (1 ml, 0.4M in tetrahydrofuran) was added. After 1 hr the reaction was allowed to evaporate to dryness before being partitioned between ethyl acetate and HCl (2M). The organics were collected and dried over magnesium sulfate, filtered and evaporated to dryness in vacuo. The residue was purified via normal phase preparatory HPLC (High Performance Liquid Chromatography) to give the title compound (56 mg).

MS: [M+H]$^+$=523

$^1$H NMR (DMSO d-6) δ 0.82(6H, d), 2.05(1H, m), 3.00(3H, s), 3.62 (2H, d), 7.41 (1H, d), 7.46 (1H, t), 7.62 (1H, t), 7.79 (1H, d).

By the method of Example 12 the following compounds were prepared:

EXAMPLE 13

3-Methyl-1-(2-methylpropyl)-5-[(1,3,4-thiadiazol-2-ylthio)methyl]-6-[[2-(trifluoromethyl)phenyl]methyl]-thieno[2,3-d]pyrimidine-2,4(1H,3H)-dione

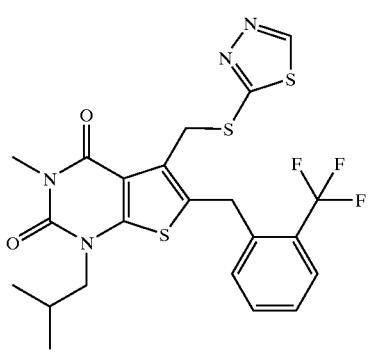

Prepared using 1,3,4-thiadiazole-2-thiol.

MS: [M+H]$^+$=527

$^1$H NMR (DMSO d-6) δ 0.84(6H, d), 2.08(1H, m), 2.99 (3H, s), 3.612 (2H, d), 7.23(1H, d), 7.48 (1H, t), 7.59 (1H, t), 7.76 (1H, d).

EXAMPLE 14

3-Methyl-1-(2-methylpropyl)-5-[[(1-methyl-1H-tetrazol-5-yl)thio]methyl]-6-[[2-(trifluoromethyl)phenyl]methyl]-thieno[2,3-d]pyrimidine-2,4(1H,3H)-dione

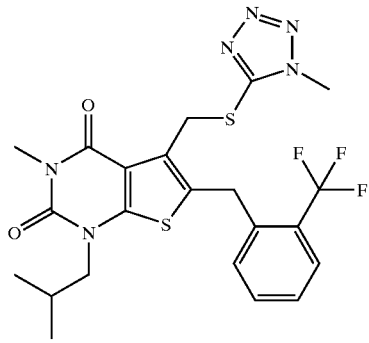

Prepared using 1-methyl-1H-tetrazole-5-thiol.

MS: [M+H]$^+$=525

$^1$H NMR (DMSO d-6) δ 0.82(6H, d), 2.08(1H, m), 2.99 (3H, s), 3.61 (2H, d), 7.24 (1H, d), 7.47 (1H, t), 7.59 (1H, t), 7.68 (1H, d).

EXAMPLE 15

5-[[(3-Chlorophenyl)thio]methyl]-3-methyl-1-(2-methylpropyl)-6-[[2-(trifluoromethyl)phenyl]methyl]-thieno[2,3-d]pyrimidine-2,4(1H,3H)-dione Prepared using 3-chloro-benzenethiol.

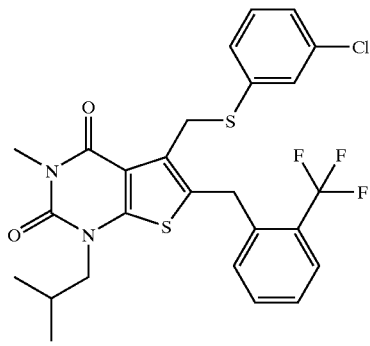

MS: [M+H]$^+$=553

$^1$H NMR (DMSO d-6) δ 0.86 (6H, d), 2.08 (1H, td), 3.25 (3H, s), 3.63 (2H, d), 4.08 (2H, s), 4.59 (2H, s), 7.22–7.74 (8H, m).

EXAMPLE 16

3-[[1,2,3,4-Tetrahydro-3-methyl-1-(2-methylpropyl)-2,4-dioxo-6-[[2-(trifluoromethyl)phenyl]methyl]-thieno[2,3-d]pyrimidin-5-yl]methoxy]-benzonitrile

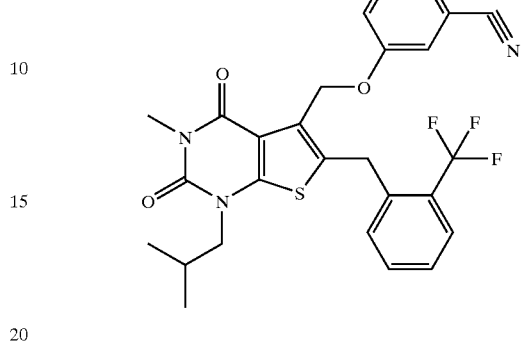

The product of Example 8 (100 mg), triphenyl phosphine (0.35 mmol), diethyl azodicarboxylate (DEAD) (0.35 mmol), 2,6-di$^t$butyl phenol (0.35 mmol) and 3-hydroxy-benzonitrile (0.47 mmol) were dissolved in tetrahydrofuran (3 ml). The reaction was allowed to stand under an atmosphere of nitrogen for 72 hrs before being allowed to evaporate to dryness. The residue was partitioned between dichloromethane and HCl (2M). The dichloromethane was collected and loaded onto silica for purification via chromatography eluting with 0 to 100% diethyl ether in isohexane to yield 63 mg of the title compound.

MS: [M+H]$^+$=528

$^1$H NMR (399.98 MHz, DMSO) δ 0.88 (d, 6H), 2.20–2.08 (m, 1H), 3.22 (s, 3H), 3.68 (d, 2H), 4.41 (s, 2H), 5.44 (s, 2H), 7.13–7.09 (m, 1H), 7.24–7.22 (m, 1H), 7.32–7.29 (m, 1H), 7.42–7.40 (m, 2H), 7.51–7.46 (m, 2H), 7.65 (t, 1H), 7.74 (d, 1H).

EXAMPLE 17

1-(Cyclopropylmethyl-3-methyl-5-(phenoxymethyl)-6-[[2-(trifluoromethyl)phenyl]methyl]-thieno[2,3-d]pyrimidine-2,4(1 H,3H)-dione

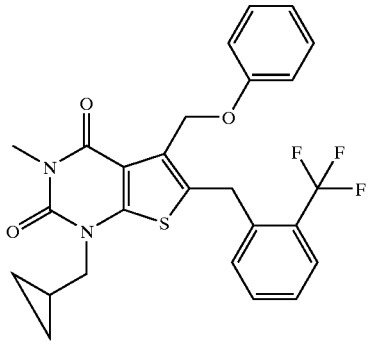

a) 1-(Cyclopropylmethyl)-1,2,3,4-tetrahydro-3-methyl-2,4-dioxo-6-[[2-(trifluoromethyl)phenyl]methyl]-thieno[2,3-d]pyrimidine-5-carboxylic acid 1-(Cyclopropylmethyl)-1,2,3,4-tetrahydro-3-methyl-2,4-dioxo-thieno[2,3-d]pyrimidine-5-carboxylic acid (6.8 g) was suspended in tetrahydrofuran (100 ml) and cooled to −78° C. to which lithium diisopropylamide (63 ml, 1M) was added. After complete addition the solution was left for 30 min before 2-(trifluoromethyl)-benzaldehyde, (7.4 mls) was added neat. After 1 h HCl(2M in water) was added and the reaction allowed to warm to room temperature. The reaction was concentrated in vacuo and partitioned between ethyl acetate and HCl (2M in water). The organic phase was collected, dried over magnesium sulfate, filtered and concentrated in vacuo and redissolved in diethyl ether, then washed with half saturated sodium hydrogen bicarbonate. The aqueous phase was collected and the diethyl ethyl was washed a seconded time with half saturated sodium hydrogen bicarbonate. The aqueous extracts were combined, acidified with HCl (conc.) and extracted with ethyl acetate. The organic phase was collected, dried over magnesium sulfate, filtered and concentrated in vacuo to brown gum. The gum was redissolved in trifluoroacetic acid (10 mls) and triethyl silane(5 mls) and stirred at room temperature for 72 hrs. The reaction was then concentrated in vacuo, and partioned between dichloromethane and water. The organics were collected, dried over magnesium sulfate, filtered and concentrated in vacuo before being purified by chromatography eluting with 20:1 dichloromethane:acetic acid and recrstallisation from ethyl acetate and isohexane, to yield 3.63 g of the subtitle compound.

MS: [M+H]$^+$=439 b) 1-(Cyclopropylmethyl)-1,2,3,4-tetrahydro-3-methyl-2,4-dioxo-6-[[2-(trifluoromethyl)phenyl]methyl]-thieno[2,3-d]pyrimidine-5-carboxylic acid, ethyl ester The product of step a) (6.63 g) was dissolved in ethanol (50 mls) and 4 drops of $H_2SO_4$ were added. The reaction mixture was heated at reflux under an atmosphere of nitrogen for 18 hrs. The reaction mixture was then concentrated in vacuo and partitioned between half saturated sodium hydrogen bicarbonate and ethyl acetate. The organics were collected, dried over magnesium sulfate, filtered and concentrated in vacuo to yield the subtitle compound (6.65 g).

MS: [M+H]$^+$=467 c) 1-(Cyclopropylmethyl)-5-(hydroxymethyl)-3-methyl-6-[[2-(trifluoromethyl)phenyl]methyl]-thieno[2,3-d]pyrimidine-2,4(1H,3H)-dione The product of step b) (6.65 g) was dissolved in tetrahydrofuran (200 mls) and LiAlH(OtBu)$_3$ (43 mls, 1M in tetrahydrofuran) was added. The reaction mixture was heated at 60° C. for 18 hrs. Water was then added and the reaction mixture was concentrated to dryness in vacuo. The residue was extracted into ethyl acetate and the solution was dried over magnesium sulphate, filtered, and concentrated in vacuo to a greenish solid which was ultrasonicated in isohexanes for 3 hrs before being collected via filtration to yield 2.76 g of the subtitle compound as a green solid.

MS: [M+H]$^+$=427 d) 1-(Cyclopropylmethyl)-3-methyl-5-(phenoxymethyl)-6-[[2-(trifluoromethyl)phenyl]methyl]-thieno[2,3-d]pyrimidine-2,4(1H,3H)-dione The product of step c) (50 mg), triphenyl phosphine (46 mg), DEAD (27 μl), 2,6-di-t-butyl phenol (36 mg) and phenol (16 mg) were dissolved in tetrahydrofuran (5 ml) and stirred at room temperature under an atmosphere of nitrogen for 18 hrs. The tetrahydrofuran was allowed to evaporate to dryness and the residue was partitioned between dichloromethane and HCl (2M). The organics were collected, dried over magnesium sulfate, filtered and concentrated in vacuo. The residue was purified by chromatography eluting with 4:1 isohexanes:diethyl ether to yield a white solid which was triturated with isohexanes to yield 14 mgs of the title compound.

MS: [M+H]$^+$=501

$^1$H NMR (DMSO) δ 0.49–0.37 (m, 4H), 2.06–1.94 (m, 1H), 3.24 (s, 3H), 3.77 (d, 2H), 4.41 (s, 2H), 5.41 (s, 2H), 6.98–6.92 (m, 3H), 7.32–7.26 (m, 2H) 7.64 (t, 1H), 7.75 (d, 1H).

EXAMPLE 18

3-Methyl-1-(2-methylpropyl)-5-[(4-oxo-1-piperidinyl)methyl]-6-[[2-(trifluoromethyl)phenyl]methyl]-thieno[2,3-d]pyrimidine-2,4(1H,3H)-dione

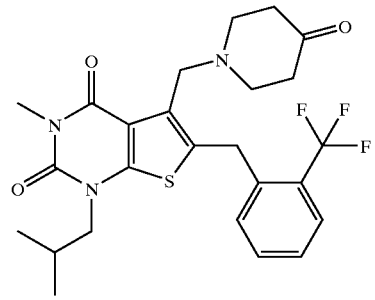

a) 5-[(4-Hydroxy-1-piperidinyl)methyl]-3-methyl-1-(2-methylpropyl)-6-[[2-(trifluoromethyl)phenyl]methyl]-thieno[2,3-d]pyrimidine-2,4(1H,3H)-dione The subtitle compound was prepared by the method of Example 9.

b) 3-Methyl-1-(2-methylpropyl)-5-[(4-oxo-1-piperidinyl)methyl]-6-[[2-(trifluoromethyl)phenyl]methyl]-thieno[2,3-d]pyrimidine-2,4(1H,3H)-dione To a solution of oxalyl chloride (523 ul) in dichloromethane (40 ml) at −78° C. under an atmosphere of nitrogen was added dropwise dimethyl sulfoxide (1.275 ml) at such a rate as to maintain a reaction mixture temperature of <−60° C. Once the dimethyl sulfoxide had been fully added, the mixture was left for 30 minutes before the crude product of step a) (2 mmols) was added as a solution in dichloromethane (2 ml). 30 minutes after full addition, triethylamine (2.63 ml) was added and the reaction was allowed to warm to room temperature.

The reaction mixture was washed with water, dried over magnesium sulfate, and then concentrated in vacuo to give the crude compound. The material was purified by chromatography eluting with 1:1 isohexane:diethyl ether to yield the title compound (81 mg).

MS: [M+H]$^+$=508

$^1$H NMR (DMSO d-6) δ 0.86(6H, d), 2.13(1H, m), 2.21(4M, m), 2.74 (4H, m), 3.24(3H, s), 3.67(2H, d), 4.00 (2H, s), 4.46(2H, s), 7.48(2H, m), 7.65 (1H, t), 7.75 (1H, d).

EXAMPLE 19

2-Hydroxy-N-[[1,2,3,4-tetrahydro-3-methyl-1-(2methylpropyl)-2,4-dioxo-6-[[2-(trifluoromethyl)phenyl]methyl]-thieno[2,3-d]pyrimidin-5-yl]methyl]-acetamide

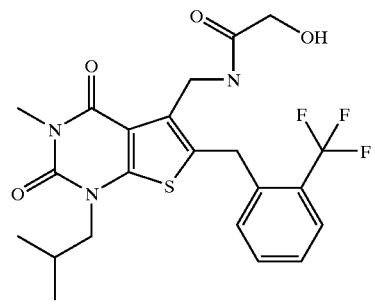

a) 5-(Aminomethyl)-3-methyl-1-(2-methylpropyl)-6-[[2-(trifluoromethyl)phenyl]methyl]-thieno[2,3-d]pyrimidine-2,4(1H,3H)-dione The product of Example 8 (100 mg) was dissolved in dichloromethane (2 ml) and thionyl chloride (52 ul) was added. After 1 hr the reaction was concentrated in vacuo and stored under a high vacuum for 1 hr. The residue was redissolved in dioxane (10 ml) and this solution was added to a preformed mixture of 880 aqueous ammonia (10 mls) and dioxane (10 ml). The mixture was stirred at room temperature for 18 hrs before being concentrated in vacuo and extracted into ethyl acetate. The organics were collected, dried over magnesium sulfate and evaporated to yield a yellow foam (98 mg).

MS: $[M+H]^+$=426 b) 2-Hydroxy-N-[[1,2,3,4-tetrahydro-3-methyl-1-(2-methylpropyl)-2,4-dioxo-6-[[2-(trifluoromethyl)phenyl]methyl]thieno[2,3-d]pyrimidine-5-yl]-methyl]-acetamide The product of step a) (98 mg), glycolic acid (19 mg), 1-(3-dimethylaminopropyl)-3-ethylcarbodiimide hydrochloride (EDCl) (47.7 mg) and 1-hydroxybenzotriazole hydrate (HOBT) (34.7 mg) were dissolved in dichloromethane (5 ml) and stirred under an atmosphere of nitrogen for 72 hrs. The mixture was then concentrated in vacuo, and the residue partitioned between ethyl acetate and HCl (2M). The organic phase was collected, dried over magnesium sulfate, and concentrated in vacuo. The residue was purified by normal phase preparatory High Pressure Liquid Chromatography (HPLC) to yield the title compound (40 mg) as a white solid.

MS: $[M+H]^+$=484

$^1$H NMR (DMSO) δ 0.85 (d, 6H), 2.14–2.07 (m, 1H), 3.28 (s, 3H), 3.65 (d, 2H), 3.79 (d, 2H), 4.48 (s, 2H), 4.50 (s, 2H), 5.59 (t, 1H), 7.35 (d, 1H), 7.48 (t, 1H), 7.61 (t, 1H), 7.76 (d, 1H), 7.93 (t, 1H).

EXAMPLE 20

1-Hydroxy-N-[[1,2,3,4-tetrahydro-3-methyl-1-(2-methylpropyl)-2,4-dioxo-6-[[2-(trifluoromethyl)phenyl]methyl]-thieno[2,3-d]pyrimidin-5-yl]methyl]-cyclopropanecarboxamide

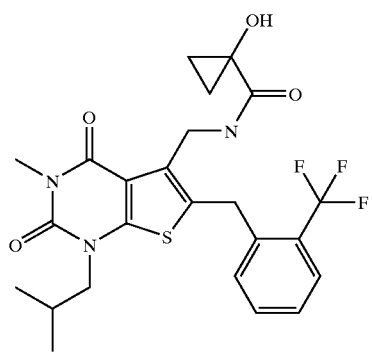

Prepared by the method of Example 19.

MS: $[M\pm H]^+$=510

$^1$H NMR (DMSO) δ 0.82 (q, 2H), 0.86 (d, 6H), 1.00 (q, 2H), 2.14–2.07 (m, 1H) 3.29 (s, 3H), 3.65 (d, 2H), 4.46 (s, 2H), 4.50 (d, 2H), 6.29 (s, 1H), 7.32 (d, 1H), 7.47 (t, 1H), 7.60 (t, 1H), 7.75 (d, 1H), 8.12 (t, IH).

EXAMPLE 21

1,2,3,4-Tetrahydro-N-(2-hydroxyethyl)-N,3-dimethyl-1-(2-methylpropyl)-2,4-dioxo-6-[[2-(trifluoromethyl)phenyl]methyl]-thieno[2,3-d]pyrimidine-5-acetamide

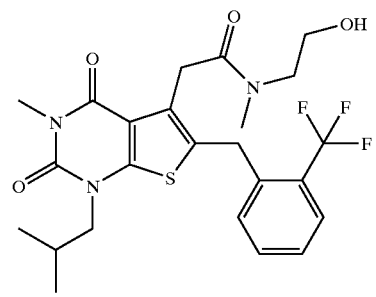

a) 5-(Diazoacetyl)-3-methyl-1-(2-methylpropyl)-6-[[2-(trifluoromethyl)phenyl]methyl]-thieno[2,3-d]-pyrimidine-2,4(1H,3H)-dione 1,2,3,4-Tetrahydro-3-methyl-1-(2-methylpropyl)-2,4-dioxo-6-[[2-(trifluoromethyl)phenyl]methyl]-thieno[2,3-d]pyrimidine-5-carboxylic acid, (prepared by the method of Example 8a) (2.534 g) was dissolved in dicloromethane (30 ml) with dimethyl formamide (1 drop) and oxalyl chloride (1 ml) was added. The reaction mixture was stirred at room temperature for 18 hrs, then concentrated in vacuo and stored under high vacuum at 60° C. for 2 hrs. The resultant yellow oil was redissolved in dichloromethane (50 ml) and triethylamine (1.51 ml) and trimethylsilyldiazomethane (6 ml of 2M solution in tetrahydrofuran) was added. The reaction was stirred for 72 hrs before being quenched by addition of dilute aqueous acetic acid. The organic phase was collected, dried over magnesium sulfate, and concentrated in vacuo. The resultant material was purified by chromatography eluting with 3:1 isohexane:ethyl acetate to yield 1.5 g of the subtitle compound.

M+H—N$_2$=437 b) 1,2,3,4-Tetrahydro-3-methyl-1-(2-methylpropyl)-2,4-dioxo-6-[[2-(trifluoromethyl)phenyl]methyl]-thieno[2,3-d]pyrimidine-5-acetic acid The product of step a) (1.5 g) was dissolved in methanol (50 ml) and Ag$_2$O (300 mg) was added. The suspension was heated at reflux under an atmosphere of nitrogen for 1 h. The mixture was then filtered, evaporated to dryness in vacuo and the residue was redissolved in tetrahydrofuran (21 ml), methanol (7 ml) and lithium hydroxide (7 ml of 1M aqueous solution) and stirred for 18 hrs. The reaction was acidified by addition of dilute HCl and extracted thrice into ethyl acetate. The combined organic phases were dried over magnesium sulphate, and concentrated in vacuo to a yellow solid which was recrystallised from ethyl acetate and isohexane to yield the subtitle compound (1.1 g).

MS: $[M+H]^+$ 455

$^1$H NMR (DMSO) δ 0.86 (d, 6H), 2.16–2.08 (m, 1H), 3.22 (s, 3H), 3.66 (d, 2H), 3.91 (s, 2H), 7.40 (d, 1H), 7.47 (t, 1H), 7.60 (t, 1H), 7.75 (d, 1H), 12.25 (s, 1H).

c) 1,2,3,4-Tetrahydro-N-(2-hydroxyethyl)-N,3-dimethyl-1-(2-methylpropyl)-2,4-dioxo-6-[[2-(trifluoromethyl)phenyl]methyl]-thieno[2,3-d]pyrimidine-5-acetamide The product of step b) (98 mg) was dissolved in 1-methyl-2-pyrrolidinone (NMP) (1 ml) to which EDCl (1 ml), HOBT (1 ml) and N-methyl ethanolamine (1 ml) was added. The reaction was stirred for 18 hrs before being concentrated in vacuo. The residue was partitioned between dichloromethane and water. The organic phase was adsorbed onto silica and purified by chromatography eluting with 0–10% methanol in dichloromethane to yield the title compound (62 mg).

MS: [M+H]⁺=512

¹H NMR (DMSO d-6) δ 0.86(6H, d), 2.08(1H, m), 3.32(3H, s), 3.46(1H,t), 3.51 (1H, t), 3.62(3H,m), 4.08(2H, s), 4.22(2H, d), 4.56 (1H, t), 4.8291H, t), 7.46(2H, m), 7.61(1H, m), 7.75(1H, d).

EXAMPLE 22

N-(2-Fluoroethyl)-1,2,3,4-tetrahydro-3-methyl-1-(2-methylpropyl)-2,4-dioxo-6-[[2-(trifluoromethyl)phenyl]methyl]-thieno[2,3-d]pyrimidine-5-acetamide

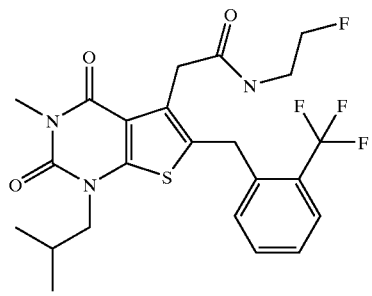

Prepared using 2-fluoro-ethanamine according to the method of Example 21.

MS: [M+H]⁺=500

¹H NMR (DMSO) δ 0.86 (d, 6H), 2.15–2.09 (m, 1H), 3.23 (s, 3H), 3.39–3.36 (m, 2H), 3.66 (d, 2H), 3.88 (s, 2H), 3.88 (s, 2H), 4.23 (t, 3H), 4.44 (t, 1H), 7.45 (s, 1H), 7.49 (t, 1H), 7.62 (t, 1H), 7.75 (d, 1H), 8.03 (t, 1H).

EXAMPLE 23

1,2,3,4-Tetrahydro-3-methyl-1-(2-methylpropyl)-β,2,4-trioxo-6-[[2-(trifluoromethyl)phenyl]methyl]-thieno[2,3-d]pyrimidine-5-propanenitrile

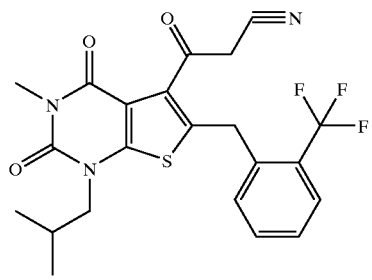

a) 5-(Chloroacetyl)-3-methyl-1-(2-methylpropyl)-6-[[2-(trifluoromethyl)phenyl]methyl]-thieno[2,3-d]pyrimidine-2,4(1H,3H)-dione 1,2,3,4-Tetrahydro-3-methyl-1-(2-methylpropyl)-2,4-dioxo-6-[[2-(trifluoromethyl)phenyl]methyl]-thieno[2,3-d]pyrimidine-5-carboxylic acid, (prepared by the method of Example 8a) (3.665 g) was suspended in dichloromethane (70 ml) containing dimethyl formamide (1 drop) and treated with oxalyl chloride (1.47 ml). 1 hr after gas evolution ceased the reaction was concentrated in vacuo and stored under high vacuum for 1 h. The residue was redissolved in dichloromethane (50 ml) and treated with triethylamine (1 ml). To this solution was added trimethylsilyldiazomethane (7 mls of 2M solution in tetrahydrofuran) and the reaction was stirred at room temperature under an atmosphere of nitrogen for 4 hrs before HCl (8 ml, 4M in dioxane) was added. The reaction was stirred for 18 hrs before being concentrated in vacuo and the residue was purified by chromatography eluting with 2:1 isohexane:diethyl ether. The product was recrystallised from ethyl acetate and isohexane to yield the subtitle compound as white needles (4.616 g)

MS: [M+H]⁺=473/5

¹H NMR (DMSO) δ 0.87 (d, 6H), 2.14–2.07 (m, 1H), 3.24 (s, 3H), 3.67 (d, 2H), 4.25 (s, 2H), 4.84 (s, 2H), 7.49 (d, 1H), 7.53 (t, 1H), 7.67 (t, 1H), 7.77 (t, 1H), b) 1,2,3,4-Tetrahydro-3-methyl-1-(2-methylpropyl)-β,2,4-trioxo-6-[[2-(trifluoromethyl)phenyl]methyl]-thieno[2,3-d]pyrimidine-5-propanenitrile The product of step a) (200 mg) was dissolved in dimethyl formamide (10 ml) and NaCN (44 mg) was added. The reaction was heated at 90° C. for 30 mins under an atmosphere of nitrogen. The reaction was partitioned between ethyl acetate and water. The organics were collected, dried over magnesium sulfate, and concentrated in vacuo. The residue was purified by preparatory normal phase HPLC to yield the title compound (107 mg).

MS: [M+H]⁺=464

¹H NMR (DMSO) δ 0.86 (d, 6H), 2.13–2.06 (m, 1H), 3.25 (s, 3H), 3.70–3.66 (m, 2H), 4.28 (s, 2H), 4.28 (s, 2H), 4.31–4.28 (m, 2H), 7.55–7.37 (m, 2H) 7.70–7.64 (m, 1H), 7.77 (d, 1H), 11.61 (d, 1H).

EXAMPLE 24

3-Methyl-1-(2-methylpropyl)-5-[(E)-2-phenylethenyl]-6-[[2-(trifluoromethyl)phenyl]methyl]-thieno[2,3-d]pyrimidine-2,4(1H,3H)-dione

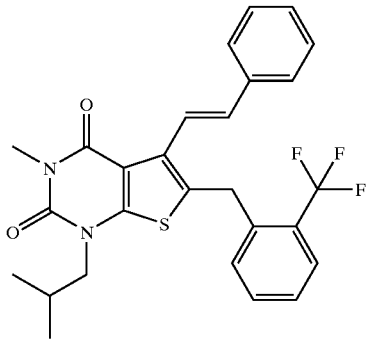

The product of Example 8 (200 mg) was dissolved in dichloromethane (10 ml) and thionyl chloride (0.5 ml) was added. The mixture was stirred for 1 hr under an atmosphere of nitrogen before being concentrated in vacuo and stored under high vacuum for 1 hr. The residue was redissolved in triethyl phosphite (5 ml) and heated at 150° C. under an atmosphere of nitrogen for 3 hrs. The vessel was fitted with a distillation head and heated under a high vacuum to remove the excess triethyl phosphite. The residue was dissolved in tetrahydrofuran (5 ml) and benzaldehyde (50 mg) was added, then the mixture was cooled to −78° C. Lithium diisopropylamide (550 ul of a 1M solution in tetrahydrofuran/hexane) was added and the cooling bath removed. After 3 hrs at room temperature benzaldehyde (50 mg) was added and after 10 mins the reaction was quenched with water, concentrated in vacuo, and the residue partitioned between ethyl acetate and water. The organic phase was dried over magnesium sulfate, filtered, and concentrated in vacuo. The material was purified via normal phase preparatory HPLC eluting with 1–25% ethyl acetate in isohexane to yield 64 mg of the title compound.

MS: [M+H]⁺=500

¹H NMR (DMSO) δ 7.79 (d, 1H), 7.70 (d, 1H), 7.67 (s, 1H), 7.52 (t, 1H), 7.44 (d, 2H), 7.40–7.36 (m, 1H), 7.30–7.25 (m, 2H), 6.75 (s, 1H), 6.71 (s, 1H), 4.51 (s, 2H), 3.68 (d, 2H), 3.26 (s, 3H), 2.16–2.10 (m, 1H), 0.88 (d, 6H).

EXAMPLE 25

Cyclopropanecarboxamide, N-[1,2,3,4-tetrahydro-3-methyl-1-(2-methylpropyl)-2,4-dioxo-6-[[2-(trifluoromethyl)phenyl]methyl]thieno[2,3-d]pyrimidin-5-yl]

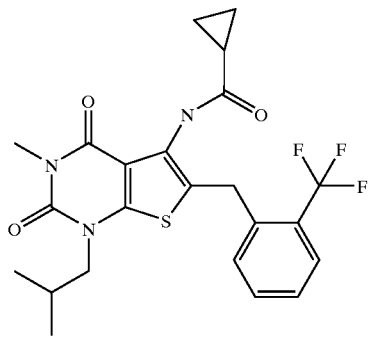

a) 5-Amino-3-methyl-1-(2-methylpropyl)-6-[[2-(trifluoromethyl)phenyl]methyl]-thieno[2,3-d]pyrimidine-2,4(1H,3H)-dione 1,2,3,4-Tetrahydro-3-methyl-1-(2-methylpropyl)-2,4-dioxo-6-[[2-(trifluoromethyl)phenyl]methyl]-thieno[2,3-d]pyrimidine-5-carboxylic acid made by the method of Example 8a) (3.316 g), triethylamine (1.38 ml) and diphenylphosphoryl azide (2.26 ml) were heated at 90° C. under an atmosphere of nitrogen in tert-butanol for 18 hrs. The reaction was concentrated in vacuo and the residue redissolved in dichloromethane (50 ml) and trifluoroacetic acid (30 ml). The mixture was allowed to stir for 36 hrs before being concentrated in vacuo, and residual acid was removed by azeotroping with toluene. The residue was partitioned between half saturated sodium hydrogen carbonate and dichloromethane. The organics were collected, dried over magnesium sulfate and concentrated in vacuo. The crude product was purified by chromatography, eluting with 2:1 isohexane:diethyl ether to yield a highly crystalline solid which was recystallised from dichloromethane/isohexane to yield the subtitle compound (1.553 g).

MS: [M+H]⁺=412 b) N-[1,2,3,4-Tetrahydro-3-methyl-1-(2-methylpropyl)-2,4-dioxo-6-[[2-(trifluoromethyl)phenyl]methyl]-thieno[2,3-d]pyrimidin-5-yl]-cyclopropanecarboxamide The product of step a) (200 mg) was dissolved in dichloromethane (2 ml) and triethylamine (130 μl) before being treated with cyclopropanecarbonyl chloride (1 ml of a 1M solution in dichloromethane). The reaction was allowed to stand for 72 hrs to produce needles of NEt₃.HCl. The reaction was washed with dil. HCl, concentrated in vacuo and the residue purified by chromatography, eluting with 0–100% diethyl ether in isohexane followed by preparatory reverse phase HPLC to yield the title compound (33 mg).

MS: [M+H]⁺=480

¹H NMR (DMSO) δ 0.78–0.76 (m, 4H), 0.86 (d, J=6.7 Hz, 6H), 1.90–1.83 (m, 1H), 2.16–2.07 (m, 1H), 3.22 (s, 3H), 3.64 (d, 2H), 4.11 (s, 2H), 7.41 (d, 1H), 7.49 (t, 1H), 7.62 (t, 1H), 7.73 (d, 1H), 9.77 (s, 1H).

EXAMPLE 26

2,2,2-Trifluoro-N-[1,2,3,4-tetrahydro-3-methyl-1-(2-methylpropyl)-2,4-dioxo-6-[[2-(trifluoromethyl)phenyl]methyl]thieno[2,3-d]pyrimidin-5-yl]-acetamide

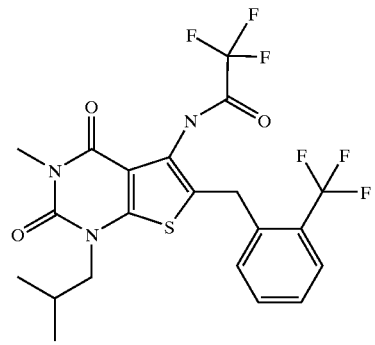

Prepared using trifluoroacetic anhydride according to the method of Example 25.

MS: [M+H]⁺=508

Boiling Point=412

¹H NMR (DMSO) δ 0.88 (d, 6H), 2.17–2.10 (m, 1H), 3.21 (s, 3H), 3.68 (d, 2H), 4.20 (s, 2H), 7.42 (d, 1H), 7.48 (t, 2H), 7.63 (t, 1H), 7.74 (d, 1H), 11.11 (s, 1H).

EXAMPLE 27

5-(Dimethylamino)-3-methyl-1-(2-methylpropyl)-6-[[2-(trifluoromethyl)phenyl]methyl]-thieno[2,3-d]pyrimidine-2,4(1H,3H)-dione

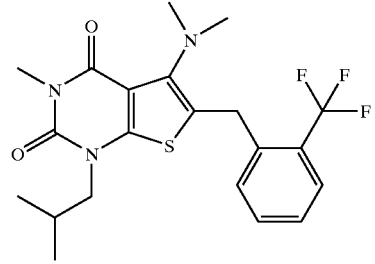

The product of Example 25 step a) (100 mg) was dissolved in 1-methyl-2-pyrrolidinone (2 ml) and methyl iodide (1 ml) was added. After 18 hrs the reaction mixture was concentrated in vacuo and the residue purified by chromatography eluting with 9:1 isohexane:diethyl ether followed by preparatory reverse phase HPLC to yield the title compound (11 mg).

MS: [M+H]⁺=440

¹H NMR (DMSO) δ 0.86 (d, 6H), 2.18–2.07 (m, 1H), 2.71 (s, 6H), 3.27 (s, 5H), 3.66 (d, 2H), 4.32 (s, 2H), 7.35 (d, 1H), 7.46 (t, 1H), 7.63 (t, 1H), 7.74 (d, 1H).

EXAMPLE 28

1,2,3,4-Tetrahydro-3-methyl-1-(2-methylpropyl)-2,4-dioxo-6-[[2-(trifluoromethyl)phenyl]methyl]-thieno[2,3-d]pyrimidine-5-propanoic acid

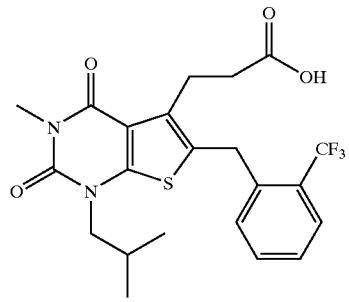

a) 1,2,3,4-Tetrahydro-3-methyl-1-(2-methylpropyl)-2,4-dioxo-6-[[2-(trifluoromethyl)phenyl]methyl]-thieno[2,3-d]pyrimidine-5-propanoic acid, methyl ester A slurry of 10% palladium on charcoal in ethanol was added to a solution of 3-[1,2,3,4-tetrahydro-3-methyl-1-(2-methylpropyl)-2,4-dioxo-6-[[2-(trifluoromethyl)phenyl]methyl]thieno[2,3-d]pyrimidin-5-yl]-2-propenoic acid, methyl ester, (2.17 g, Example 3 step a)) in ethanol (75 ml) and hydrogenated at 4 bar for 48 hours. The solution was filtered through a glass fibre filter and the filtrate concentrated under reduced pressure. The residue was purified by flash silica chromatography eluting with 1% ethanol in dichloromethane to give the sub-title compound as a white solid (1.27 g).

m.p. 86–88° C.

MS(APCI) 483[M+H]$^+$ $^1$HNMR(CDCl$_3$) δ 0.95(6H,d); 2.20–2.29(1H,m); 2.69 (2H,t); 3.20(2H,t); 3.41(3H,s); 3.65(3H,s); 3.70(2H,d); 4.32 (2H,s); 7.18(1H,d); 7.36(1H,t); 7.47(1H,t); 7.69(1H,d).

b) 1,2,3,4-Tetrahydro-3-methyl-1-(2-methylpropyl)-2,4-dioxo-6-[[2-(trifluoromethyl)phenyl]methyl]-thieno[2,3-d]pyrimidine-5-propanoic acid The product of step a) (1.09 g), lithium hydroxide monohydrate (0.19 g) and water (10 ml) in tetrahydrofuran (30 ml) were stirred at room temperature for 2 hours. Evaporation and purification of the residue by flash silica chromatography eluting with a gradient of 0–2% ethanol in dichloromethane gave the title compound as a white solid (0.81 g).

m.p. 165–167° C.

MS(APCI) 469[M+H]$^+$ $^1$HNMR(CDCl$_3$) δ 0.94(6H,d); 2.25(1H,septet); 2.72(2H, t); 3.19(3H,t); 3.42(3H,s); 3.70(2H,d); 4.31(2H,s); 7.17(1H, d); 7.36(1H,t); 7.47(1H,t); 7.69(1H,d).

EXAMPLE 29

5-(3-Hydroxypropyl)-3-methyl-1-(2-methylpropyl)-6-[[2-(trifluoromethyl)phenyl]methyl]-thieno[2,3-d]pyrimidine-2,4(1H,3H)-dione

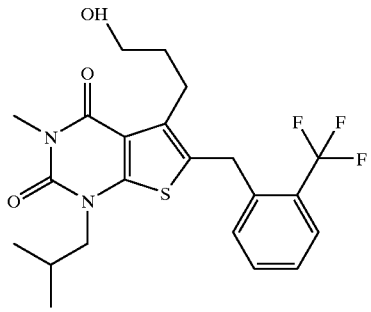

The product of Example 28 (674 mg) was dissolved in tetrahydrofuran (20 ml) and LiAlH(O$^t$Bu)$_3$ (4 ml of 1M solution in tetrahydrofuran) was added. The mixture was heated at 55° C. under an atmosphere of nitrogen for 17 hrs. The reaction was quenched with water, concentrated in vacuo and purified via chromatography, eluting with 1:1 diethyl ether:isohexane to give the title compound (392 mg).

MS: [M+H]$^+$=455

$^1$H NMR (DMSO) δ 0.86 (d, 6H), 1.69–1.62 (m, 2H), 2.16–2.09 (m, 1H), 2.88–2.85 (m, 2H), 3.24 (s, 3H), 3.40 (q, 2H), 3.65 (d, 2H), 4.29 (s, 2H), 4.44 (t, 1H), 7.34 (d, 1H), 7.48 (t, 1H), 7.64 (t, 1H), 7.76 (d, 1H).

EXAMPLE 30

5-[(2-Fluorophenyl)hydroxymethyl]-3-methyl-1-(2-methylpropyl)-6-[[2-(trifluoromethyl)phenyl]methyl]-thieno[2,3-d]pyrimidine-2,4(1H,3H)-dione

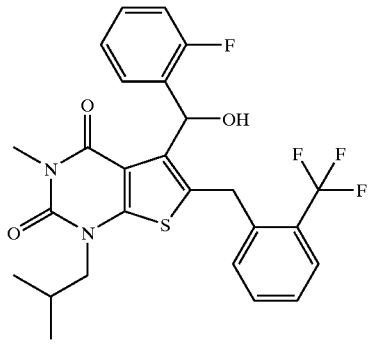

5-Bromo-1-isobutyl-3-methyl-6-[2-(trifluoromethyl) benzyl]-thieno[2,3-d]pyrimidine-2,4(1H,3H)-dione (Example 1 part c)) (100 mg) was dissolved in tetrahydrofuran (2 mls) and EtMgBr (250 ul of 1M solution in tetrahydrofuran) was added. After 10 mins 2-fluorobenzaldehyde (250 ul of a 1M solution in tetrahydrofuran) was added. After 1 hr the reaction was quenched via addition of water. The reaction was concentrated in vacuo and extracted into dichloromethane, concentrated in vacuo and the residue purified via chromatography eluting with 0–100% diethyl ether in isohexane to yield the title compound (9 mg).

M+H—H$_2$O=503

$^1$H NMR (DMSO) δ 0.85 (d, J=6.7 Hz, 6H), 2.15–2.08 (m, 1H), 3.24 (s, 1H), 3.68–3.65 (m, 3H), 4.45–4.26 (m,

3H), 6.39 (d, 1H), 6.89 (d, 1H), 7.10–7.05 (m, 2H), 7.16 (d,1H), 7.26–7.22 (m, 1H), 7.47–7.41 (m, 1H), 7.54–7.50 (m, 2H), 7.69 (d, 1H).

EXAMPLE 31

5-(2-Fluorobenzoyl)-3-methyl-1-(2-methylpropyl)-6-[[2-(trifluoromethyl)phenyl]methyl]-thieno[2,3-d]pyrimidine-2,4(1H,3H)-dione

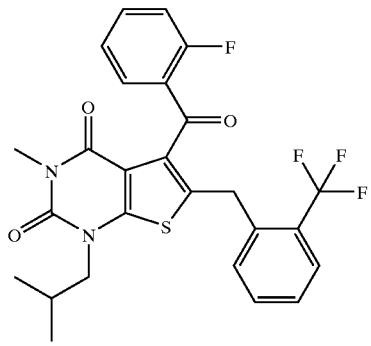

5-Bromo-1-isobutyl-3-methyl-6-[2-(trifluoromethyl)benzyl]thieno[2,3-d]pyrimidine-2,4(1H,3H)-dione (Example 1 part c)) (100 mg) was dissolved in tetrahydrofuran (2 ml) and EtMgBr (210 ul of a 1M solution in tetrahydrofuran) was added. After 10 min 2-fluorobenzaldehyde (210 μl of a 1M solution in tetrahydrofuran) was added. After 1 hr the reaction was quenched via addition of water. The reaction was concentrated in vacuo and extracted into dichloromethane, concentrated in vacuo and purified by chromatography eluting with 0–75% diethyl ether in isohexane to yield 5-[(2-fluorophenyl)hydroxymethyl]-3-methyl-1-(2-methylpropyl)-6-[[2-(trifluoromethyl)phenyl]methyl]-thieno[2,3-d]pyrimidine-2,4(1H,3H)-dione. This was redissolved in dichloromethane (1 ml) and added to a mixture of oxalyl chloride (50 ul) and dimethyl sulphoxide (100 μl) in dichloromethane (1 ml) at −78° C. After 30 mins triethylamine (260 ul) was added and the reaction allowed to warm to room temperature. The reaction was then washed with water and evaporated to dryness before the residue was purified by chromatography eluting with 0–75% diethyl ether in hexane to yield the title compound (11 mg).

MS: [M+H]$^+$=519

$^1$H NMR (DMSO) δ 0.90 (d, 6H), 2.19–2.12 (m, 1H), 3.11 (s, 3H), 3.70 (d, 2H), 4.23 (s, 2H), 7.30–7.24 (m, 2H), 7.50–7.44 (m, 2H), 7.66–7.62 (m, 2H), 7.71–7.67 (m, 2H).

EXAMPLE 32

Inhibition of PMA/Ionomycin-Stimulated Peripheral Blood Mononuclear Cell Proliferation The assay for PMA/ionomycin-stimulated PBMC proliferation was performed in 96-well flat bottomed microtitre plates. Compounds were prepared as 10 mM stock solutions in dimethyl sulfoxide. A 50-fold dilution of this was prepared in RPMI and serial dilutions were prepared from this solution. 10 μl of the 50-fold diluted stock, or dilutions of it, were added to the well to give concentrations in the assay starting at 9.5 μM and going down. Into each well was placed 1×10$^5$ PBMC, prepared from human peripheral blood from a single donor, in RPMI1640 medium supplemented with 10% human serum, 2 mM glutamine and penicillin/streptomycin. Phorbol myristate acetate (PMA) (0.5 ng/ml final concentration) and ionomycin (500 ng/ml final concentration) were added to these cells in supplemented RPMI1640 medium (as above) so that the final volume of the assay was 0.2 ml. The cells were incubated at 37° C. in a humidified atmosphere at 5% carbon dioxide for 72 hours. $^3$H-Thymidine (0.5 μCi) was added for the final 6 hours of the incubation. The level of radioactivity incorporated by the cells was then determined and this is a measure of proliferation.

The title compounds of Examples 1 to 31 were found to exhibit an IA$_{50}$ value of less than 1×10$^{-6}$ M in the above test.

What is claimed is:

1. A compound of formula

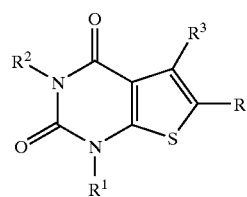

(I)

wherein:

R is —C(O)Ar$^1$, —C(R$^4$)(R$^5$)Ar$^1$ or Ar$^3$;

Ar$^1$ represents a 5- to 10-membered aromatic ring system wherein up to 3 ring atoms may be heteroatoms independently selected from nitrogen, oxygen and sulphur, the ring system being optionally substituted by one or more substituents independently selected from C$_{1-4}$ alkyl, C$_{1-4}$ alkoxy, halogen, trifluoromethyl, hydroxy, nitro, cyano, NR$^6$R$^7$ and —CH$_2$NR$^8$R$^9$;

R$^1$ and R$^2$ each independently represent a hydrogen atom, C$_{1-6}$ alkyl, C$_{3-6}$ alkenyl, CH$_2$C$_{3-5}$ cycloalkyl or C$_{3-6}$ cycloalkyl;

R$^3$ represents a group X—R$^{10}$ or Ar$^2$;

X represents a bond or a group NR$^{11}$;

Ar$^2$ represents a 5- or 6-membered aromatic ring wherein up to 4 ring atoms may be heteroatoms independently selected from nitrogen, oxygen and sulphur, the ring being optionally substituted by one or more substituents independently selected from C$_{1-4}$ alkyl, C$_{1-4}$ alkoxy, C$_{1-4}$ alkylthio, acetyl, halogen, trifluoromethyl, hydroxy, hydroxyl, amino, nitro, cyano and benzyl;

R$^4$ represents a hydrogen atom or C$_{1-4}$ alkyl;

R$^5$ represents a hydrogen atom or hydroxyl group;

R$^6$ and R$^7$ each independently represent a hydrogen atom or C$_{1-4}$ alkyl, or together form an alkylene chain which together with the nitrogen atom to which they are attached forms a 5- to 7-membered saturated heterocyclic ring;

R$^8$ and R$^9$ each independently represent a hydrogen atom or C$_{1-4}$ alkyl, or R$^8$ and R$^9$ together form an alkylene chain which with the nitrogen atom to which they are attached forms a 5- to 7-membered saturated heterocyclic ring;

R$^{10}$ represents C$_{1-6}$ alkyl, C$_{2-6}$ alkenyl or C$_{2-6}$ alkynyl, each of which may be optionally substituted by one or more substituents independently selected from carboxyl, hydroxyl, —C(O)—R$^{12}$, C$_{3-6}$ cycloalkyl, morpholinyl, —NR$^{13}$R$^{14}$, —SR$^{15}$, —OR$^{16}$, phenyl and halophenyl, or R$^{10}$ represents a C$_{3-6}$ cycloalkylcarbonyl, —C(O)CH$_2$CN, halophenylcarbonyl or trifluoromethylcarbonyl group;

$R^{11}$ represents a hydrogen atom or a $C_{1-6}$ alkyl group;

$R^{12}$ represents piperazinyl optionally substituted by a $C_{1-6}$ alkyl group, or $R^{12}$ represents a group —$NR^{17}R^{18}$;

$R^{13}$ and $R^{14}$ each independently represent a hydrogen atom, or a $C_{1-4}$ alkyl, $C_{1-4}$ hydroxyalkyl or —C(O)—$R^{19}$ group, or $R^{13}$ and $R^{14}$, together form an alkylene chain which with the nitrogen atom to which they are attached, forms a 5- to 7-membered saturated heterocyclic ring which may be optionally substituted by one or more substituents independently selected from $C_{1-4}$ alkyl, hydroxyl and oxo;

$R^{15}$ and $R^{16}$ each independently represent a 5- or 6-membered aromatic ring wherein up to 4 ring atoms may be heteroatoms independently selected from nitrogen, oxygen and sulphur, the ring being optionally substituted by one or more substituents independently selected from halogen atoms, cyano and $C_{1-4}$ alkyl;

$R^{17}$ and $R^{18}$ each independently represent a hydrogen atom, or a $C_{1-4}$ alkyl group optionally substituted by one or more substituents independently selected from halogen atoms and hydroxyl;

$R^{19}$ represents a $C_{1-6}$ alkyl or $C_{3-6}$ cycloalkyl group, each of which may be optionally substituted by a hydroxyl group; and $Ar^3$ represents acenaphthenyl, indanyl or fluorenyl, each of which may be optionally substituted by one or more substituents independently selected from $C_{1-4}$ alkyl, $C_{1-4}$ alkoxy, halogen and trifluoromethyl;

or a pharmaceutically acceptable salt thereof.

2. A compound according to claim 1, wherein R represents —$C(R^4)(R^5)Ar^1$.

3. A compound according to claim 1, wherein $Ar^1$ represents phenyl, naphthyl, pyrazolyl, thienyl, oxazolyl, imidazolyl, pyridinyl, pyridopyrrolyl, benzimidazolyl, indazolyl, benzothiazolyl, benzoxazolyl, thipzolyl or benzotriazolyl, each of which may be optionally substituted by one to four substituents independently selected from $C_{1-4}$ alkyl, $C_{1-4}$ alkoxy, halogen, trifluoromethyl, hydroxy, nitro, cyano, $NR^6R^7$ and —$CH_2NR^8R^9$.

4. A compound according to claim 1, wherein $R^1$ and $R^2$ each independently represent a $C_{1-4}$ alkyl group.

5. A compound according to claim 1, wherein $R^3$ represents a group $R^{10}$ and X represents a bond.

6. A compound of formula (I) according to claim 1 being:

5-(3-Hydroxy-3-methyl-1-butynyl)-1-isobutyl-3-methyl-6-[2-(trifluoromethyl)benzyl]-thieno[2,3-d]pyrimidine-2,4(1H,3H)-dione, 3-Methyl-5-[3-(4-methyl-1-piperazinyl)-3-oxo-1-propenyl]-1-(2-methylpropyl)-6-[[2-(trifluoromethyl)phenyl]methyl]-thieno[2,3-d]pyrimidine-2,4(1H,3H)-dione, 3-[1,2,3,4-Tetrahydro-3-methyl-1-(2-methylpropyl)-2,4-dioxo-6-[[2-(trifluoromethyl)phenyl]methyl]-thieno[2,3-d]pyrimidin-5-yl]-2-propenoic acid, 5-[3-Hydroxy-3-methyl-1-butenyl]-3-methyl-1-(2-methylpropyl)-6-[[2-(trifluoromethyl)phenyl]methyl]-thieno[2,3-d]pyrimidine-2,4(1H,3H)-dione, (E) and (Z)-5-[2-cyclopentylethenyl]-3-methyl-1-(2-methylpropyl)-6-[[2-(trifluoromethyl)phenyl]methyl]-thieno[2,3-d]pyrimidine-2,4(1H,3H)-dione, 3-Methyl-1-(2-methylpropyl)-5-(3-thienyl)-6-[[2-(trifluoromethyl)phenyl]methyl]-thieno[2,3-d]pyrimidine-2,4(1H,3H)-dione, 5-(5-Acetyl-2-thienyl)-3-methyl-1-(2-methylpropyl)-6-[[2-(trifluoromethyl)phenyl]methyl]-thieno[2,3-d]pyrimidine-2,4(1H,3H)-dione, 5-(Hydroxymethyl)-3-methyl-1-(2-methylpropyl)-6-[[2-(trifluoromethyl)phenyl]methyl]-thieno[2,3-d]pyrimidine-2,4(1H,3H)-dione, 3-Methyl-1-(2-methylpropyl)-5-(4-morpholinylmethyl)-6-[[2-(trifluoromethyl)phenyl]methyl]-thieno[2,3-d]pyrimidine-2,4(1H,3H)-dione, 5-[(4-Hydroxy-3-methyl-1-piperidinyl)methyl]-3-methyl-1-(2-methylpropyl)-6-[[2-(trifluoromethyl)phenyl]methyl]-thieno[2,3-d]pyrimidine-2,4(1H,3H)-dione, 5-[[(2-Hydroxyethyl)methylamino]methyl]-3-methyl-1-(2-methylpropyl)-6-[[2-(trifluoromethyl)phenyl]methyl]-thieno[2,3-d]pyrimidine-2,4(1H,3H)-dione, 3-Methyl-5-[[(2-methyl-3-furanyl)thio]methyl]-1-(2-methylpropyl)-6-[[2-(trifluoromethyl)phenyl]methyl]-thieno[2,3-d]pyrimidine-2,4(1H,3H)-dione, 3-Methyl-1-(2-methylpropyl)-5-[(1,3,4-thiadiazol-2-ylthio)methyl]-6-[[2-(trifluoromethyl)phenyl]methyl]-thieno[2,3-d]pyrimidine-2,4(1H,3H)-dione, 3-Methyl-1-(2-methylpropyl)-5-[[(1-methyl-1H-tetrazol-5-yl)thio]methyl]-6-[[2-(trifluoromethyl)phenyl]methyl]-thieno[2,3-d]pyrimidine-2,4(1H,3H)-dione, 5-[[(3-Chlorophenyl)thio]methyl]-3-methyl-1-(2-methylpropyl)-6-[[2-(trifluoromethyl)phenyl]methyl]-thieno[2,3-d]pyrimidine-2,4(1H,3H)-dione, 3-[[1,2,3,4-Tetrahydro-3-methyl-1-(2-methylpropyl)-2,4-dioxo-6-[[2-(trifluoromethyl)phenyl]methyl]-thieno[2,3-d]pyrimidin-5-yl]methoxy]-benzonitrile, 1-(Cyclopropylmethyl)-3-methyl-5-(phenoxymethyl)-6-[[2-(trifluoromethyl)phenyl]methyl]-thieno[2,3-d]pyrimidine-2,4(1H,3H)-dione, 3-Methyl-1-(2-methylpropyl)-5-[(4-oxo-1-piperidinyl)methyl]-6-[[2-(trifluoromethyl)phenyl]methyl]-thieno[2,3-d]pyrimidine-2,4(1H,3H)-dione, 2-Hydroxy-N-[[1,2,3,4-tetrahydro-3-methyl-1-(2-methylpropyl)-2,4-dioxo-6-[[2-(trifluoromethyl)phenyl]methyl]-thieno[2,3-d]pyrimidin-5-yl]methyl]-acetamide, 1-Hydroxy-N-[[1,2,3,4-tetrahydro-3-methyl-1-(2-methylpropyl)-2,4-dioxo-6-[[2-(trifluoromethyl)phenyl]methyl]-thieno[2,3d]pyrimidin-5-yl]methyl]-cyclopropanecarboxamide, 1,2,3,4-Tetrahydro-N-(2-hydroxyethyl)-N,3-dimethyl-1-(2-methylpropyl)-2,4-dioxo-6-[[2-(trifluoromethyl)phenyl]methyl]-thieno[2,3-d]pyrimidine-5-acetamide, N-(2-Fluoroethyl)-1,2,3,4-tetrahydro-3-methyl-1-(2-methylpropyl)-2,4-dioxo-6-[[2-(trifluoromethyl)phenyl]methyl]-thieno[2,3-d]pyrimidine-5-acetamide, 1,2,3,4-Tetrahydro-3-methyl-1-(2-methylpropyl)-β,2,4-trioxo-6-[[2-(trifluoromethyl)phenyl]methyl]-thieno[2,3-d]pyrimidine-5-propanenitrile, 3-Methyl-1-(2-methylpropyl)-5-[(E)-2-phenylethenyl]-6-[[2-(trifluoromethyl)phenyl]methyl]-thieno[2,3-d]pyrimidine-2,4(1H,3H)-dione, Cyclopropanecarboxamide, N-[1,2,3,4-tetrahydro-3-methyl-1-(2-methylpropyl)-2,4-dioxo-6-[[2-(trifluoromethyl)phenyl]methyl]thieno[2,3-d]pyrimidin-5-yl], 2,2,2-Trifluoro-N-[1,2,3,4-tetrahydro-3-methyl-1-(2-methylpropyl)-2,4-dioxo-6-[[2-(trifluoromethyl)phenyl]methyl]thieno[2,3-d]pyrimidin-5-yl]-acetamide, 5-(Dimethylamino)-3-methyl-1-(2-methylpropyl)-6-[[2-(trifluoromethyl)phenyl]methyl]-thieno[2,3-d]pyrimidine-2,4(1H,3H)-dione, 1,2,3,4-Tetrahydro-3-methyl-1-(2-methylpropyl)-2,4-dioxo-6-[[2-(trifluoromethyl)phenyl]methyl]-thieno[2,3-d]pyrimidine-5-propanoic acid, 5-(3-Hydroxypropyl)-3-methyl-1-(2-methylpropyl)-6-[[2-(trifluoromethyl)phenyl]methyl]-thieno[2,3-d]pyrimidine-2,4(1H,3H)-dione, 5-[(2-Fluorophenyl)hydroxymethyl]-3-methyl-1-(2-methylpropyl)-6-[[2-(trifluoromethyl)phenyl]methyl]-thieno[2,3-d]pyrimidine-2,4(1H,3H)-dione, 5-(2-Fluorobenzoyl)-3-methyl-1-(2-methylpropyl)-6-[[2-(trifluoromethyl)phenyl]methyl]-thieno[2,3-d]pyrimidine-2,4(1H,3H)-dione, or a pharmaceutically acceptable salt of any one thereof.

7. A process for the preparation of a compound of formula (I) as defined in claim 1 which comprises, (a) when $R^3$ represents $Ar^2$, reacting a compound of formula

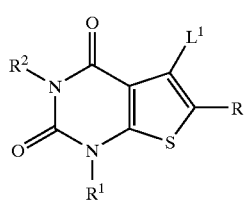

(II)

wherein $L^1$ represents a leaving group and R, $R^1$ and $R^2$ are defined as in formula (I), with a (hetero)aromatic boronic acid of formula

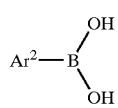

(III)

wherein $Ar^2$ is defined as in formula (I), in the presence of a palladium (0) species; or (b) when $R^3$ represents $X-R^{10}$, X represents a bond and $R^{10}$ represents a $C_{2-6}$ alkenyl or alkynyl group optionally substituted as defined in formula (I), reacting a compound of formula (II) as defined in (a) above with a compound of formula (IV), $R^{10'}-H$, wherein $R^{10'}$ represents a $C_{2-6}$ alkenyl or alkynyl group optionally substituted as defined in $R^{10}$ of formula (I) which comprises a terminal carbon-carbon double or triple bond, in the presence of a palladium (II) species and optionally either a copper (I) species or a coordinating ligand; or (c) when $R^3$ represents $X-R^{10}$, X represents a bond and $R_{10}$ represents a $C_{2-6}$ alkyl group optionally substituted as defined in formula (I), reacting a corresponding compound of formula (I) in which $R^{10}$ represents a $C_{2-6}$ alkenyl or alkynyl group optionally substituted as defined in formula (I) with hydrogen in the presence of a palladium or platinum catalyst; or (d) when $R^3$ represents $X-R^{10}$, X represents a bond and $R^{10}$ represents a $C_{3-6}$ cycloalkylcarbonyl, $-C(O)CH_2CN$, halophenylcarbonyl or trifluoromethylcarbonyl group, reacting a compound of formula (II) as defined in (a) above, with a suitable Grignard reagent and then with a compound of formula (V), $R^{10''}-H$, wherein $R^{10''}$ represents a $C_{3-6}$ cycloalkylcarbonyl, $-C(O)CH_2CN$, halophenylcarbonyl or trifluoromethylcarbonyl group, followed by an oxidation reaction; or (e) when $R^3$ represents $X-R^{10}$ and X represents a group $NR^{11}$, reacting a compound of formula

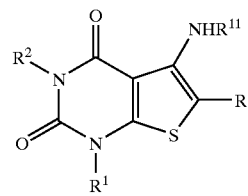

(VI)

wherein R, $R^1$, $R^2$ and $R^{11}$ are as defined in formula (I), with a compound of formula (VII), $R^{10}-L^2$, wherein $L^2$ represents a leaving group and $R^{10}$ is as defined in formula (I); or (f) when $R^3$ represents $X-R^{10}$, X represents a bond and $R^{10}$ represents $CH_2CO_2H$, reacting a compound of formula

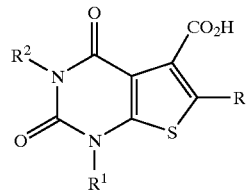

(VIII)

wherein R, $R^1$ and $R^2$ are as defined in formula (I), with an activating agent followed by diazomethane, and causing the resulting intermediate to undergo a Wolff rearrangement in the presence of a metal oxide catalyst to obtain a compound of formula (I);

and optionally after (a), (b), (c), (d), (e) or (f) converting the compound of formula (I) obtained to a further compound of formula (I) and/or forming a pharmaceutically acceptable salt of the compound of formula (I).

8. A pharmaceutical composition comprising a compound of formula (I) or a pharmaceutically acceptable salt thereof according to claim 1 in association with a pharmaceutically acceptable adjuvant, diluent or carrier.

9. A process for the preparation of a pharmaceutical composition as claimed in claim 8 which comprises mixing a compound of formula (I) or a pharmaceutically acceptable salt thereof according to claim 1 with a pharmaceutically acceptable adjuvant, diluent or carrier.

10. A method of effecting immunosuppression which comprises administering to a patient a therapeutically effective amount of a compound of formula (I) or a pharmaceutically acceptable salt thereof as claimed in claim 1.

11. A method of treating, or reducing the risk of, an airways disease in a patient suffering from, or at risk of, said disease, which comprises administering to the patient a therapeutically effective amount of a compound of formula (I) or a pharmaceutically acceptable salt thereof as claimed in claim 1.

* * * * *